US010449224B2

(12) United States Patent
Christofidou-Solomidou

(10) Patent No.: US 10,449,224 B2
(45) Date of Patent: *Oct. 22, 2019

(54) FLAXSEED LIGNAN COMPLEX, METHODS OF USING AND COMPOSITIONS THEREOF

(75) Inventor: Melpo Christofidou-Solomidou, Eagleville, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 673 days.

This patent is subject to a terminal disclaimer.

(21) Appl. No.: 12/601,882

(22) PCT Filed: May 27, 2008

(86) PCT No.: PCT/US2008/006694
§ 371 (c)(1),
(2), (4) Date: Jun. 1, 2010

(87) PCT Pub. No.: WO2008/147563
PCT Pub. Date: Dec. 4, 2008

(65) Prior Publication Data
US 2010/0239696 A1 Sep. 23, 2010

Related U.S. Application Data

(60) Provisional application No. 60/924,678, filed on May 25, 2007.

(51) Int. Cl.
*A61K 36/55* (2006.01)
(52) U.S. Cl.
CPC .................................. *A61K 36/55* (2013.01)
(58) Field of Classification Search
None
See application file for complete search history.

(56) References Cited

U.S. PATENT DOCUMENTS

| | | | |
|---|---|---|---|
| 6,407,075 B1 | 6/2002 | Scott et al. | |
| 6,486,126 B1 | 11/2002 | Prasad | |
| 6,673,773 B2 * | 1/2004 | Prasad | 514/25 |
| 2003/0100514 A1 * | 5/2003 | Ahotupa | A61K 31/05 514/22 |
| 2006/0052438 A1 | 3/2006 | Ho et al. | |
| 2006/0148732 A1 | 7/2006 | Gutterman et al. | |
| 2007/0087063 A1 | 3/2007 | Bland et al. | |

FOREIGN PATENT DOCUMENTS

| | | |
|---|---|---|
| JP | 2005278429 | 10/2005 |
| WO | WO 0078771 A1 * | 12/2000 |
| WO | WO 02/092073 | 11/2002 |

OTHER PUBLICATIONS

Mohammad Kabiruddin. "Laooq Katan" from Bayaaz-e-Kabir, vol. II (Compiled), Daftar al-Maseeh. Karol Bagh, New Delhi, 1938 AD, p. 149.*
Prasad, Kailash. "Hypocholesterolemic and antiatherosclerotic effect of flax lignan complex isolated from flaxseed". Atherosclerosis 179 (2005) 269-275.*
Kinniery et al. "Dietary Flaxseed Supplementation Ameliorates Inflammation and Oxidative Tissue Damage in Experimental Models of Acute Lung Injury in Mice". J. Nutr. vol. 136 (2006) 1545-1551.*
Daniells, S. "Flaxseed could boost lung health, animal study". Internet publication Date: May 24, 2006 [Retrieved on: Jun. 10, 2012]. Retrieved from the Internet: <URL: http://www.nutraingredients.com/Research/Flaxseed-could-boost-lung-health-animal-study>.*
(U1) Rickhard. Internet Date: Jul. 4, 2004. [Retrieved from the Internet on: Dec. 22, 2015]. Retrieved from: <URL: http://www.healthboards.com/boards/asthma/187463-no-flovent-since-third-day-eating-boiled-ground-flax-seed.html>.*
(V1) Muir et al., ed. Pingally et al. "Human Health" From "Flax from the Genus *Linum*" (2003), pp. bottom of 261-262.*
(W1) Lee et al. The FASEB Journal. 2007;21:899.1.*
(X1) Lee et al. The FASEB Journal. 2007;21:365.4.*
Govt of India; Ayurvedic Formulary of India—Part H, Govt of India, Ministry of Health & Family Welfare, Dcptt. Of1.S.M. &H., New Delhi, Edn. 1st [This book contains back references from 1000 B.C. to 20th century] p.69, (2000).
Ziya Al-Din Abdullah Ibn Al-Baitar; AMaam'e-ii-Mufradaat-al-Advia-w ai-Aghzia, vol. I (3th century AD), Matba Amra, Cairo, Egypt, p. 90, 1874 AD.
Mohammad Azarn Khan; Muheet-e-Azam vol. IV (Part I) {19th ccntury AD), Matba Nizami, Kanpur, p. 35, 1899 AD.
Ali Ibn-e-Abbaas Majoosi; Kaamil-al-Sena'ah, Part II (10$^{th}$ century AD), Central Council for Research in Unani Medicine, 61-65 Institutional Area, Janak Puri, New Delhi-58, 2005 AD, p. 54.
Mohammad Akbar Arzani; Qaraabaadeen Qaadri (17$^{th}$ century AD), Ahmade Publication, Delhi, 1968 AD, p. 131.
Abu Bakr Mohammad.Bin Zakariyya Al-Razi; Kitaab-al-Haawi-fil-Tibb, vol. IV (9$^{th}$ century AD), Dayerah-al-Ma'aarif Usmania, Hyderabad, 1978 AD, p. 90.
Abu Bakr Mohammad.Bin Zakariyya Al-Razi; Kitaab-al-Haawi-fil-Tibb, vol. IV (9$^{th}$ century AD), Dayerah-al-Ma'aarif Usmania, Hyderabad, 1978 AD, p. 198.
Abu Ali Ibn-e-Sina; Al-Qaanoon-fil-Tibb, vol. V (11$^{th}$ century AD), Publication Department, Jamia Hamdard, New Delhi-62, 1996 AD, p. 199.
Abu Bakr Mohammad.Bin Zakariyya Al-Razi; Kitaab-al-Haawi-fil-Tibb, vol. IV (9$^{th}$ century AD), Dayerah-al-Ma'aarif Usmania, Hyderabad, 1978 AD, pp. 25-147.

(Continued)

*Primary Examiner* — Amy L Clark
(74) *Attorney, Agent, or Firm* — Mark S. Cohen; Pearl Cohen; Zedek Latzer Baratz LLP

(57) ABSTRACT

This invention relates to methods and compositions for treating pathological lung conditions using whole-grain flaxseed or flaxseed lignans (isolated in form of the lignan precursor Secoisolariciresinol diglucoside (SDG) directly from whole-grain flaxseed or chemically synthesized directly into the mammalian, readily metabolizable forms, Enterodiol (ED) or Enterolactone (EL). Such pathological condition result from oxidative lung injury such as ischemia-reperfusion injury (related to lung transplantation), radiation fibrosis and cancer. Specifically, the invention is directed to the use of flaxseed lignans in the treatment of acute and chronic lung injury as well as cancer.

5 Claims, 30 Drawing Sheets

(56) References Cited

OTHER PUBLICATIONS

Abu Bakr Mohammad.Bin Zakariyya Al-Razi; Kitaab-al-Haawi-fil-Tibb, vol. IV (9th century AD), Dayerah-al-Ma'aarif Usmania, Hyderabad, 1978 AD, pp. 25-26.

Kinniry, P, et al. Dietary flaxseed supplementation ameliorates inflammation and oxidative tissue damage in experimental models of acute lung injury in mice. J. Nutrition, 2006, vol. 136, No. 6, pp. 1545, 1546, 1548, 1549.

J.C. Lee, F. Bhora, S. Chatterjee, C. Solomides, E. Arguiri, G. Cheng, and _M. Christofidou-Solomidou:_ Dietary flaxseed enhances antioxidant defenses and is protective in a mouse model of lung ischemia-reperfusion injury. /Am J Physiol Lung Cell Mol Physiol. /294(2):L255-65, 2008.

J. C. Lee, R. Krochak, A. Blouin, E. Arguiri, S.Kanterakis, A.Vachani, C.C. Solomides, K.A. Cengel and _M. Christofidou-Solomidou__:_ Dietary Flaxseed Prevents Radiation-Induced Oxidative Lung Damage Inflammation and Fibrosis In A Mouse Model Of Thoracic Radiation Injury. /Cancer Biology & Therapy/, 8(1):47-53, 2009.

Muzykantov et al. "Targeting of superoxide dismutase and catalase to vascular endothelium" Journal of Controlled Release vol. 71, Issue 1, pp. 1-21, Mar., 12, 2001.

Kozower, B.D., M. Christofidou-Solomidou, T.D. Sweitzer, S. Muro, D.G. Buerk, C.C. Solomides, S.M. Albelda, G.A. Patterson, and V.R. Muzykantov. 2003. Immunotargeting of catalase to the pulmonary endothelium alleviates oxidative stress and reduces acute lung transplantation injury. *Nat Biotechnol* 21:392-398.

Wakabayashi, N., Itoh, K., Wakabayashi, J., Motohashi, H., Noda, S., Takahashi, S., Imakado, S., Kotsuji, T., Otsuka, F., Roop, D.R., Harada, T., Engel, J.D., and Yamamoto, M. (2003). Keap1-null mutation leads to postnatal lethality due to constitutive Nrf2 activation. Nat Genet 35, 238-245.

Ikeda, T., Y. Nishijima, H. Shibata, Y. Kiso, K. Ohnuki, T. Fushiki, and T. Moritani. 2003. Protective effect of sesamin administration on exercise-induced lipid peroxidation. *Int J Sports Med* 24:530-534.

Prasad, K., S.V. Mantha, A.D. Muir, and N. D. Westcott. 1998. Reduction of hypercholesterolemic atherosclerosis by CDC-flaxseed with very low alpha-linolenic acid. *Atherosclerosis* 136:367-375.

Pattanaik, U., and K. Prasad. 1998. Oxygen Free Radicals and Endotoxic Shock: Effect of Flaxseed. *J Cardiovasc Pharmacol Ther* 3:305-318.

Mayo Clinic Staff, "Lung Cancer", Internet publication date: Apr. 17, 2012; Retrieved from the Internet: http://www.mayoclinic.com/health/lung-cancer/DS00038/METHOD=print&DSECTION=all.

Eldridge, L., "What is pulmonary pneumonitis?", Internet publication date: Feb. 25, 2011; Retrieved from the Internet: http://www.lungcancer.about.com/od/treatmentoflungcancer/a/radpneumonitis.htm?p=1.

Inskip et al., "Lung cancer risk and radiation dose among women treated for breast cancer", J. Natl. Cancer Inst. Jul. 6, 1994, 86(13): 983-8.

"American Institute for Cancer Research", AICR ScienceNow, vol. 8 (Fall 2006). Retrieved from the internet on Apr. 16, 2013 from URL: http://preventcancer.aicr.org/site/News2?page=NewsArticle&id=11325&news_iv_ctrl=0&abbr=res_>.

Kinniry et al., "Dietary flaxseed supplementation ameliorates inflammation and oxidative tissue damage in experimental models of acute lung injury in mice", J. Nutr. Jun. 2006: 136(6): 1545-1551.

\* cited by examiner

Figure 11
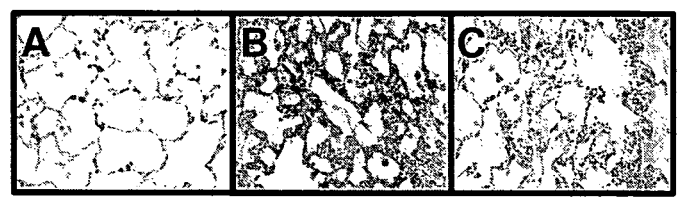
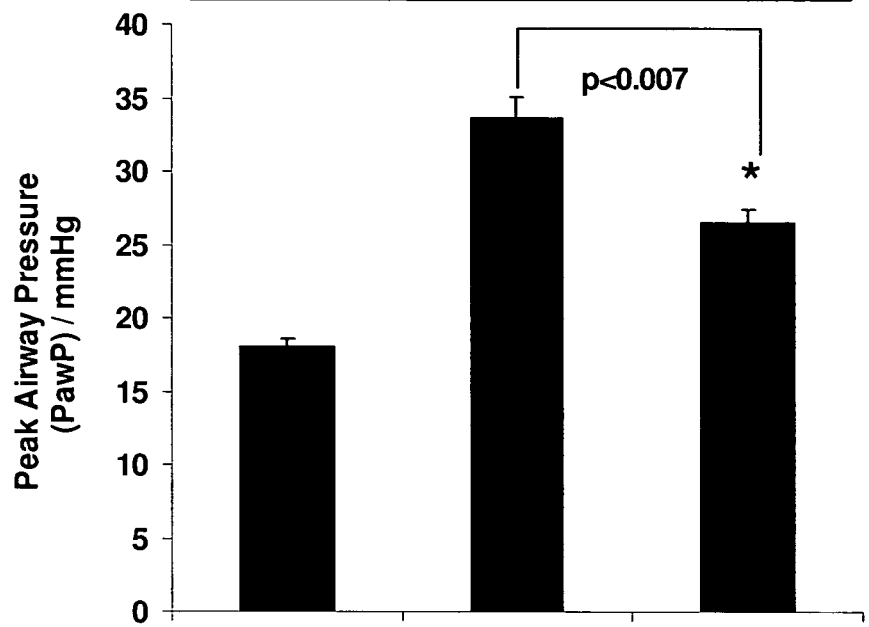
Figure 12

(Top)

(top)

(bottom)

FLAXSEED LIGNAN COMPLEX, METHODS OF USING AND COMPOSITIONS THEREOF

CROSS-REFERENCE TO RELATED APPLICATIONS

This is a national phase application of PCT patent application PCT/US08/06694, filed May 27, 2008, that claims priority to U.S. provisional patent application 60/924,678, filed May 25, 2007, both of which are incorporated by reference herein in their entirety.

FIELD OF INVENTION

This invention is directed to methods and compositions for treating pathological lung conditions using whole-grain flaxseed or flaxseed lignans (isolated in form of the lignan precursor Secoisolariciresinol diglucoside (SDG) directly from whole-grain flaxseed or chemically synthesized directly into the mammalian, readily metabolizable forms, Enterodiol (ED) or Enterolactone (EL). Such pathological condition result from oxidative lung injury such as ischemia-reperfusion injury (related to lung transplantation), radiation fibrosis and cancer. Specifically, the invention is directed to the use of flaxseed lignans in the treatment of acute and chronic lung injury as well as cancer.

BACKGROUND OF THE INVENTION

It has long been recognized that when oxygenation is restored in hypoxic tissues (re-oxygenation), hypoxic tissue injury is further augmented, a process called ischemia-reperfusion injury (MI). This mechanism of cellular injury is especially prominent in surgical, myocardial, hepatic, intestinal, cerebral, renal, and other ischemic syndromes and occurs, with varying degrees of severity, after all forms of organ transplantation. Vascular oxidative stress is also a major cause of pulmonary and systemic pathology in conditions including Acute Lung Injury (ALI/ARDS), inflammatory lung conditions, sepsis, hyperoxia and radiation injury.

Vascular I/R is responsible for acute graft failure and delayed complications of organ transplantation and cardiopulmonary bypass, as well as necrotic and apoptotic tissue injury in acute myocardial infarction (AMI), stroke, thrombosis and other cases of occlusive ischemia of vessels that perfuse blood to internal organs or extremities.

Oxidative stress in general, is characterized by the formation of reactive oxygen species (ROS) such as superoxide anion, hydrogen peroxide, and hydroxyl radical. These molecules are highly reactive and react with structures such as DNA, key cellular proteins, and the lipid component of the cell membrane leading to lipid peroxidation and subsequent cell injury that can be detected by increased permeability, and in more severe cases to cell lysis. The generation of intracellular ROS occurs in most lung parenchymal cells, such as endothelial cells, Type II alveolar epithelial cells, Clara cells, alveolar epithelial cells as well as in alveolar macrophages (See FIG. 1—taken from Muzykantov, V. R. 2001. Targeting of superoxide dismutase and catalase to vascular endothelium. *J Controlled Release* 71:1-21).

There are at least two important mechanisms for ROS production during IRI. During anoxia, hypoxanthine accumulates and the enzyme xanthine dehydrogenase is converted into xanthine oxidase, This is followed by the degradation of hypoxanthine into superoxide which occurs during reoxygenation. The other mechanism depends on the NADPH oxidase system, which is present mainly on the membrane surface of neutrophils and monocytes/macrophages and endothelial cells and catalyzes the reduction of oxygen into hydrogen peroxide and superoxide anion. Classically, it has been thought that such activated neutrophils contribute to vascular reperfusion injury, although cellular injury is propagated in the absence of inflammatory cells through mechanisms involving reactive oxygen (ROS) or nitrogen species (RNS).

In addition to leukocyte ROS, generation of ROS throby endothelial cells through this pathway also appears to be important. Studies from our group and others indicate that vascular oxidative stress induced by ROS, (including superoxide anion and $H_2O_2$) plays a key role in ischemia-reperfusion (I/R) injury. Endothelial cells (EC), which line the luminal surface of blood vessels and control vascular tone, transport of blood components to tissues and maintain blood fluidity) represent a main target of ROS in I/R. EC dysfunction and damage induced by ROS thus play a key role in the initiation and propagation of I/R injury (see FIG. 1).

Ironically, intracellular ROS produced by EC themselves in response to ischemia (endogenous ROS production) help to initiate the injurious I/R cascade, while extracellular ROS (exogenous ROS production) released from activated white blood cells (WBC) augment and further propagate the vicious cycle and subsequent pathological reactions including WBC adherence, thrombosis, vascular edema and vasoconstriction, i.e., events initiated by EC damage.

Given this pathophysiology, many believe that I/R injury could be ameliorated or even prevented by effective ROS detoxification, thus justifying the interest in the development of antioxidant prophylaxis and therapies. Conventional antioxidants such as N-acetyl-cysteine (a precursor for a main cellular reducing agent, glutathione), selected vitamins (e.g., tocopherol) and food supplements (flavonoids) afford some degree of protection in selected cases of modest chronic oxidative stress. However, the potency of these antioxidants has not been sufficient to protect against severe acute and sub-acute forms of vascular oxidative stress, such as I/R. More effective approaches are therefore needed.

Correspondingly, lung transplantation has become an important therapy for many end-stage lung diseases. Unfortunately, due to the circulatory disruption required by transplantation, a significant cause of early morbidity and mortality associated with this procedure is ischemia-reperfusion-induced injury (IRI) of the lung. Oxidative stress, the key mediator of IRI, typically manifests itself within the first 72 hours after transplantation and is characterized by alveolar damage, lung edema, and hypoxemia. Despite advances in our understanding of the mechanisms of IRI, and improvements in the technique of lung preservation, in surgical techniques and in perioperative care, up to 15% of all transplanted lungs will end up with primary graft failure. Better ways to deliver potent and safe antioxidant agents are clearly needed.

The usefulness of thoracic radiotherapy is greatly limited by the sensitivity of the lung tissue to irradiation doses necessary to eradicate malignant cells. Clinically significant radiation lung injury, such as pneumonia-like inflammation and late stage fibrosis, occurs in up to 30% of patients irradiated for lung cancer and about 10-15% of other thoracic oncology patients. The need, however, to protect "normal" lung parenchyma from unacceptable radiation injury compromises the ability to deliver tumoricidal radiotherapy doses and contributes to the high local recurrence rates experienced by lung cancer patients following definitive radiotherapy. The cytotoxic effects of ionizing radiation in normal lung parenchyma are mediated by the generation of reactive oxygen species (ROS) and propagated by ROS-driven oxidative stress thus identifying a central role of tissue antioxidant defense. A safe radioprotecting agent that would ameliorate radiation toxicity while not protecting tumor, or even preferably radiosensitizing tumor cells is desperately needed. We and others have shown that antioxidant enzyme therapy alleviates radiation-induced fibrotic lung disease. NF-E2-related factor 2 (Nrf2), a key transcriptional regulator for antioxidant response element (ARE) mediates induction of cellular antioxidant and detoxifying enzymes. Preliminary data obtained from an exploratory R21 award showed that whole grain dietary flaxseed (FS) boosts Nrf2-mediated antioxidant defense in murine lungs. Importantly, dietary whole-grain FS ameliorated the adverse effects of thoracic radiation by enhancing survival and blocking lung fibrosis while, remarkably inhibiting lung tumor growth and metastasis. We have evidence to believe that the bioactive ingredient(s) in the FS grain that mediate these effects are the lignans. Flaxseed contains the lignan precursor secoisolariciresinol diglucoside (SDG) which is metabolized in the intestine to mammalian lignans which are safe, compounds with known antioxidant, anti-inflammatory and anticarcinogenic effects. Our group discovered that chemically synthesized, commercially available flaxseed lignans, activate the Nrf2/ARE pathway mediating transcription of antioxidant enzyme genes and inhibit lung cancer cell proliferation in vitro. Additional evidence revealed proteasomal inhibition as a potential mechanism of their action. We, therefore, believe that coordinate induction of Nrf2/ARE regulated antioxidant genes by flaxseed lignans may be a novel therapeutic strategy to alleviate radiation pneumonopathy and that these agents are responsible for inhibition of lung tumor growth and metastasis.

SUMMARY OF THE INVENTION

In one embodiment, the invention provides a method of reducing acute lung inflammation, oxidative lung tissue injury or chronic lung fibrosis in a subject comprising the step of administering to said subject a composition comprising whole grain flaxseed, a bioactive ingredient or a metabolite thereof, whereby the bioactive flaxseed component or its metabolite(s) activates a transcription factor which modulates expression of protective enzymes, thereby reducing inflammation and oxidative tissue injury.

Flaxseed used in the studies contains 11.8 mg/g SDG, i.e., 1.18%. It is important to note that SDG can be extracted from whole grain flaxseed in 99.9% pure form using complex chromatography methodologies and this has been reported by many labs (refs). Alternatively, SDG can be extracted as part of a flaxseed lignan complex, enriched by 35% SDG content. This has been marketed by Archer Daniels Midland Inc (ADM) as Beneflax®. None of the data included here was derived from feeding Beneflax or purified SDG. We have used whole grain diet or mammalina lignans ED and EL from a commercially available source (Chromadex Inc, Ca.).

In another embodiment, provided herein is a method of chemopreventing cancer in a subject, comprising the step of administering to the subject an effective amount of a flaxseed lignan complex, thereby modulating the regulation of genes mediated by the Nrf2/ARE pathway, inducing the expression of endogenous carcinogenic drug metabolizing enzymes.

In one embodiment, provided herein is a method of treating lung cancer in a subject, comprising increasing dietary intake of whole-grain flaxseed or flaxseed lignans (isolated from wholegrain or chemicallly synthesized) by the subject, thereby inhibiting proteasome activity and tumor growth.

In another embodiment, provided herein is a method of modulating the Nrf2/ARE pathway in a cell, increasing expression of endogenous drug metabolizing enzymes, comprising contacting the cell with an effective amount of a flaxseed lignans, or its metabolite, thereby activating the Nrf2 transcription factor.

In one embodiment, provided herein is a composition for modulating the Nrf2/ARE pathway in a subject, comprising increasing dietary intake of whole-grain flaxseed or flaxseed lignans (isolated from wholegrain or chemicalily synthesized).

BRIEF DESCRIPTION OF THE DRAWINGS

The invention will be better understood from a reading of the following detailed description taken in conjunction with the drawings in which like reference designators are used to designate like elements, and in which:

FIG. 11: shows Flaxseed-treated rats showed decreased lung inflammation and interstitial edema (C) associated with the procedure (orthotopic lung transplantation) as compared to rats fed a normal chow (B) while (A) is an untreated control lung.

FIG. 12: shows that peak lung pressures is significantly improved in flaxseed-fed rats that underwent orthotopic lung transplantation.

DETAILED DESCRIPTION OF THE INVENTION

Figure 1:
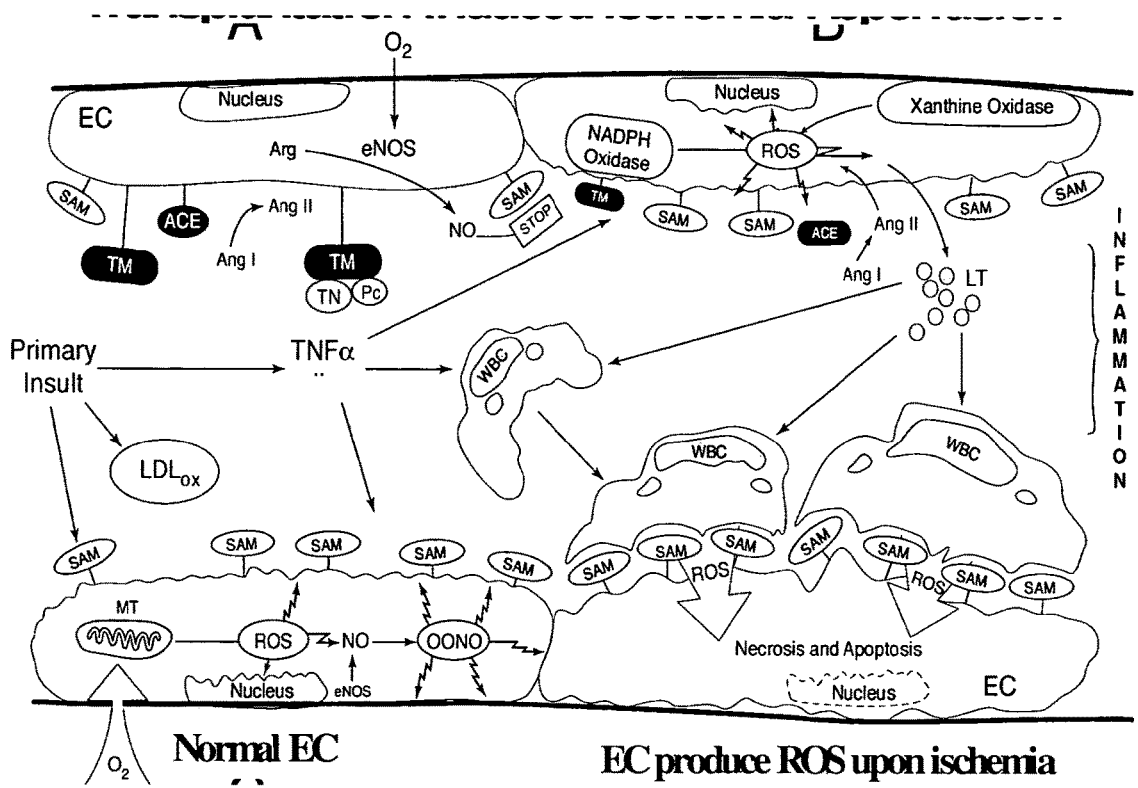
FIG. 1: shows endothelial cell oxidative stress in lung transplantation-induced ischemia reperfusion; taken from Muzykantov, V. R. 2001. Targeting of superoxide dismutase and catalase to vascular endothelium. *J Controlled Release* 71:1-21).

This invention relates in one embodiment to methods and compositions for treating pathological conditions resulting from ischemia-reperfusion using Flaxseed. In another embodiment, the invention is directed to the use of flaxseed lignan complex in the treatment of ischemia-reperfusion-injury.

In one embodiment, the term "ischemia-reperfusion injury (IRI)" refers to the process occurring when oxygenation is restored in hypoxic tissues (re-oxygenation), further augmenting hypoxic tissue injury. This mechanism of cellular injury is prominent in one embodiment, in surgical circumstances, or myocardial, hepatic, intestinal, cerebral, renal, and other ischemic syndromes in other embodiments, and occurs in another embodiment, with varying degrees of severity, after all forms of organ transplantation. In another embodiment, vascular oxidative stress is a major cause of pulmonary and systemic pathology in conditions including Acute Lung Injury (ALI/ARDS) in one embodiment, or inflammatory lung conditions, sepsis, hyperoxia and radiation injury in other embodiments. In another embodiment "Ischemia" or an "ischemic event" refers to an insufficient supply of blood to a specific cell, tissue or organ. A consequence of decreased blood supply is in another embodiment, an inadequate supply of oxygen to the organ or tissue (hypoxia). Prolonged hypoxia result in one embodiment, in an injury to the affected organ or tissue.

In one embodiment, the term "Anoxia" refers to a virtually complete absence of oxygen in the organ or tissue, which, if prolonged, may result in death of the cell, organ or tissue. In another embodiment, the term "Hypoxia" or a "hypoxic condition" refers to condition under which a cell, organ or tissue receives an inadequate supply of oxygen. In one embodiment, the term "Ischemic injury" refers to cellular and/or molecular damage to an organ or tissue or cell as a result of a period of ischemia. In another embodiment, the term "Hypoxic injury" refers to damage to a cell, organ, or tissue due to a period of inadequate oxygen supply. In one embodiment, the term "Reperfusion" refers to return of fluid flow into a tissue after a period of no-flow or reduced flow. For example in one embodiment, in reperfusion of the heart, fluid or blood returns to the heart through a supply line, such as the coronary arteries in vivo, after removal of an occlusion to the fluid or blood supply.

Flaxseed is grown in one embodiment, for its oil content for use primarily as an industrial oil. In another embodiment, flax is a rich source of fatty acids and has increasing uses in foods. In another embodiment, lignans, a component of Flaxseed refer in another embodiment to dimers containing a dibenzylbutane skeleton. When part of the human diet, such compounds are converted in another embodiment into mammalian lignans known as enterolactone (EL) and in another embodiment, to enterodiol (ED). In one embodiment, whole flaxseed flour and its defatted meal are the highest mammalian lignan producers, the meal and flour being 75 times higher than the next ranking entry, a seaweed, and over 100 times greater than most common foodstuffs. The principal lignan found in flaxseed is secoisolariciresinol diglucoside, referred to in certain embodiments, as SDG.

Flaxseed contains in one embodiment, 40% by weight fat ("linseed oil"). De-fatted (hexane-extracted) flax seed contains a residue of about 2% by wt. fat, with the remainder comprising: 46% by wt. fiber (both water-soluble fiber or "mucilage," acidic heterogeneous polysaccharides that contain galacturonic acid, galactose, rhamnose, and xylose, comprising 30-40% of the total fiber present, and water-insoluble fiber, which comprises 60-70% of the total fiber present); 10% total other carbohydrates, including lignans; 35% by wt. protein; 6-7% ash. In another embodiment, free SDG do not occur in the de-fatted flaxseed but is liberated by alkaline hydrolysis of various ester-linked polymers. In one embodiment, the available SDG in de-fatted flaxseed ranges from 0.9% to 3.0% by wt.

In one embodiment, Flaxseed (FS) is a useful antioxidant nutrient having high contents of omega-3 fatty acids and lignans that help reduce inflammation in one embodiment, and is helpful in treating a variety of cardiovascular and autoimmune diseases in other embodiments. Lignans, referring in another embodiment to widely occurring plant compounds that are closely related to lignin possess in another embodiment antioxidant properties. Secoisolariciresinol diglucoside (SDG) isolated from FS, is metabolized in the mammalian intestine to the lignans enterodiol (ED), and enterolactone (EL). In one embodiment, the oxygen radical scavenging properties of the FS lignans are operable in vitro by either direct hydroxyl radical scavenging activity, or by inhibition of lipid peroxidation in another embodiment. In one embodiment, due to the ability of lignans to act as platelet-activating-factor (PAF) antagonists, the lignan SDG exerts antioxidant activity by inhibiting reactive oxygen species (ROS) production by white blood cells.

Accordingly and in one embodiment, provided herein is a method of reducing acute lung inflammation, oxidative lung tissue injury or chronic lung fibrosis in a subject comprising administering to said subject a composition comprising a whole grain flaxseed, a bioactive ingredient or a metabolite thereof, whereby the bioactive flaxseed component or its metabolite(s) activates a transcription factor which modulates expression of protective enzymes, whereby in another embodiment the bioactive compound is whole grain flaxseed or an entire flaxseed lignan component(FLC).

In one embodiment, the intrapulmonary deposition of Endotoxin (LPS) from Gram-negative bacteria simulates bacterial pneumonia, a mode of injury characterized in one embodiment, by an intense local inflammatory response associated with diffuse neutrophilic infiltrate and cell damage that evolves over several days. In another embodiment, intratracheal instillation of bacterial LPS, simulating the effects of bacterial pneumonia, results in ALI within just 24 hours. In another embodiment, LPS activates alveolar macrophages and causes early infiltration of neutrophils further exacerbating the injury. In one embodiment, acid aspiration results in a dramatic increase of lung permeability, associated with WBC influx of predominantly PMN in the BAL. In another embodiment, aspiration of gastric contents causes acute lung injury/acute respiratory distress syndrome (ALI/ARDS). Aspiration of gastric contents has been modeled in one embodiment, in mice by intratracheal instillation of hydrochloric acid. Aspirated HCl evoke in another embodiment, direct damage to the alveolar-capillary membrane and promote PMN adhesion, activation, and sequestration. In addition, HCL aspiration has been associated with thromboxane synthesis and generation of oxygen radicals associated with PMN activation. In another embodiment, the methods provided herein, using the compositions provided herein are effective for the treatment, or in another embodiment, in inhibiting or suppressing, or in yet another embodiment, in reducing the symptoms associated with acute lung inflammation, oxidative lung tissue injury or chronic lung fibrosis in a subject.

In one embodiment, the methods of treating acute lung inflammation, oxidative lung tissue injury or chronic lung fibrosis in a subject as provided herein, comprise contacting the subject with a composition comprising a whole grain flaxseed, a bioactive ingredient or a metabolite thereof, whereby the bioactive compound is whole grain flaxseed or flaxseed lignan metabolites.

In one embodiment, the primary lignan found in flaxseed is 2,3-bis (3-methoxy-4-hydroxybenzyl)butane-1,4-diol (secoisolariciresinol), which is stored in another embodiment as the conjugate secoisolariciresinol diglucoside (SDG) in its native state in the plant. In another embodiment, flaxseed contains levels of phytoestrogens which are 75-800 times greater than any other plant food. The plant lignan, catecholic nordihydroguaiaretic acid, is a potent antioxidant and is used in one embodiment in the compositions and methods provided herein.

In one embodiment, the whole grain flaxseed or flaxseed lignan complex (FLC) used in the methods and compositions provided herein, for treating acute lung inflammation, oxidative lung tissue injury or chronic lung fibrosis in a subject comprises the plant lignan precursor, secolsolariciresinol diglucoside (SDG). In another embodiment, the whole grain flaxseed or flaxseed lignan metabolites comprises the mammalian lignans enterodiol. In another embodiment, the whole grain flaxseed or flaxseed lignan metabolites comprises enterolactone, or in another embodiment, the whole grain flaxseed or flaxseed lignan metabolites comprises a combination thereof.

In another embodiment, provided herein is a method of reducing acute lung inflammation, oxidative lung tissue injury or chronic lung fibrosis in a subject comprising increasing dietary intake of a bioactive flaxseed component by the subject of the compositions provided herein, which in one embodiment comprise a whole grain flaxseed, a bioactive ingredient or a metabolite thereof, whereby the bioactive flaxseed component or its metabolite(s) activates a transcription factor which modulates expression of protective enzymes, thereby reducing inflammation and oxidative tissue injury, whereby the inflammation or lung fibrosis is the result of acute or oxidative lung injury.

In one embodiment, the transcription factor which modulates expression of protective enzymes, which is activated by the administration of the compositions provided herein, which include in another embodiment the whole grain flaxseed or flaxseed lignan complex (FLC), used in the method provided herein, of reducing acute lung inflammation, oxidative lung tissue injury or chronic lung fibrosis in a subject is nuclear factor E2-related factor 2 (Nrf2).

In one embodiment, Nrf2 is a "master" antioxidant transcription factor regulating many endogenous antioxidant enzymes such as hemeoxygenase I in one embodiment, or GST, NQO-1, acetyltransferase, sulfotransferase or their combination in another embodiment. In one embodiment, the transcription factor Nrf2 binds to and activates a specific "antioxidant response element" (ARE) in the promoter region of detoxifying and anti-oxidant enzyme genes. Under homeostatic conditions Nrf2 is bound in one embodiment, by a Keap1 protein, which in another embodiment, keeps the complex in the cytoplasm; In one embodiment, electrophiles and reactive oxygen species liberate Nrf2 from Keap1 and induce the translocation and accumulation of Nrf2 in the nucleus. Once in the nucleus, binding of nrf2 to the antioxidant response element (ARE) drives the induction of a gene groups that in another embodiment, facilitate the detoxification of carcinogens, or enhance the reducing potential against electrophiles and free radicals, and elevate cellular capacity for repair/removal of oxidatively damaged proteins, or their combination in other embodiments.

In another embodiment, Flaxseed lignans used in the compositions provided herein, for the methods provided herein, act directly or in one embodiment indirectly, on nrf2, inducing its translocation to the nucleus and in one embodiment, activating of the ARE-regulated transcription. In one embodiment nrf2 is required or sufficient in one embodiment, to induce endogenous antioxidant enzyme (AOE) enhancement.

Accordingly, provided herein is a method of reducing acute lung inflammation, oxidative lung tissue injury or chronic lung fibrosis in a subject comprising administering to said subject a composition comprising a whole grain flaxseed, a bioactive ingredient or a metabolite thereof, whereby the bioactive flaxseed component or its metabolite(s) activates a transcription factor which modulates expression of protective enzymes, thereby reducing inflammation and oxidative tissue injury, whereby the protective enzyme is Glutathione —S— transferase, N-acetyl transferase or other Nrf2-modulated enzymes.

In one embodiment, the methods provided herein, are effective in the chemoprevention of cancer, by in another embodiment, modulating the regulation of genes mediated by the Nrf2/ARE pathway, inducing the expression of an endogenous carcinogenic drug metabolizing enzymes. Accordingly, provided herein is a method of chemopreventing cancer in a subject, comprising the step of administering to the subject an effective amount of a flaxseed lignan metabolites, thereby modulating the regulation of genes mediated by the Nrf2/ARE pathway, inducing the expression of an endogenous carcinogenic drug metabolizing enzymes.

Lung cancer is the leading cause of cancer death in both men and women in the U.S., and cigarette smoking is a major etiologic factor. In fact, approximately 85% of lung cancer is caused by smoking. Major lung carcinogens in tobacco smoke are polycyclic aromatic hydrocarbons, typified in one embodiment by benzo[a]pyrene (BaP), and the tobacco-specific nitrosamine 4 (methylnitrosamino)-1-(3pyridyl)-1-butanone (NNK). In one embodiment flaxseed, because of its unique nutrient profile has a potential to affect the course of cardiovascular disease and some hormone-responsive cancers such as prostate cancer in one embodiment, or breast cancer in another embodiment. Flaxseed or its bioactive compounds, are effective in another embodiment in lung cancer therapy or chemoprevention. due to the activation of the Nrf2/ARE pathway (manuscript in prep) in one embodiment. The Nrf2 transcription factor regulates in one embodiment the expression of Phase II enzymes required for the detoxification of potent carcinogens, by binding in another embodiment, to the antioxidant response element (ARE), a DNA segment located upstream from antioxidant and Phase II carcinogen detoxification enzyme genes. In another embodiment, flaxseed lignans boost endogenous carcinogen detoxification systems in cells in response to a known carcinogen. In another embodiment, the effects of the whole grain flaxseed or flaxseed lignan metabolites used in the compositions disclosed herein; are mediated by modulation of the Nrf2/ARE pathway. In another embodiment, whole grain flaxseed or flaxseed lignan metabolites comprises of the plant lignan precursor, seciosolariciresinol diglucoside (SDG), or the mammalian lignans enterodiol, enterolactone, or a combination thereof are chemopreventive agents in carcinogen-induced lung carcinogenesis. In one embodiment, induction of endogenous drug metabolizing enzymes such as the Phase II Enzymes is a successful strategy for cancer chemoprevention and the hole grain flaxseed or flaxseed lignan metabolites comprises of the plant lignan precursor, seciosolariciresinol diglucoside (SDG), or the mammalian lignans enterodiol, enterolactone, or a combination thereof. encompassed in the compositions provided herein, are likely safe and easy to administer candidates in cancer prevention by modulating the regulation of genes mediated by the Nrf2/ARE pathway.

In one embodiment, the whole grain flaxseed or flaxseed lignan metabolites, through the action of the lignans, activate nrf2 inducing in another embodiment, dissociation from Keap1 and nuclear translocation and subsequent binding to the ARE, driving in one embodiment, the transcription of phase II, detoxifying enzymes leading to a more effective chemoprevention using the methods provided herein, with the compositions provided herein, which comprise in another embodiment, the whole grain flaxseed or flaxseed lignan metabolites comprises of the plant lignan precursor, seciosolariciresinol diglucoside (SDG), or the mammalian lignans enterodiol, enterolactone, or a combination thereof. In one embodiment, the cancer treated using the methods for chemoprevention provided herein, is lung cancer, bronchogenic adenocarcinoma or in another embodiment, mesothelioma-related lung cancer. In one embodiment, the endogenous antioxidant and drug detoxifying enzymes leading to a more effective chemoprevention using the methods provided herein, are glutathione S-transferase (GST), NAD(P)H:quinone oxidoreductase1 (NQO-1), epoxide hydrolase, glutamylcysteine synthetase, UDP:glucuronosyl transferases other Phase II metabolizing enzymes or a combination thereof.

Accordingly and in one embodiment, provided herein is a method of treating lung cancer in a subject, comprising increasing dietary intake of flaxseed lignan metabolites by the subject, thereby inhibiting proteasome activity. In another embodiment, provided herein is a method of treating lung cancer in a subject, comprising increasing dietary intake of flaxseed lignan metabolites by the subject, thereby inhibiting tumor growth. In another embodiment, the ubiquitin-proteasome pathway plays a critical role in the degradation of cellular proteins and cell cycle control. In another embodiment, mitotic processes are strictly regulated by cyclins and cyclin-dependent kinases which in turn are important substrates of the proteasomal degradation pathway. Inhibitors of proteasomal activity induce in another embodiment apoptosis in tumor cells and in another embodiment, are useful as anticancer agents, alone or in combination with other drugs. In one embodiment, the method of treating lung cancer in a subject, comprising increasing dietary intake of flaxseed lignan metabolites by the subject, thereby inhibiting proteasome activity and tumor growth comprises inhibiting proteasomal activity.

In another embodiment, the method of treating lung cancer in a subject, comprising increasing dietary intake of flaxseed lignan metabolites by the subject, thereby inhibiting proteasome activity and tumor growth, further comprising administering to the subject another proteasome inhibitor, such as Velcade (PS-341) and PS-519, proteasome inhibitory (+)-lactacystin β-lactone analogs, (Benzyloxycarbonyl)-Leu-Leu-phenylalaninal, Z-LLL-CHO, 2,3,5a,6-Tetrahydro-6-hydroxy-3(hyroxymethyl)-2, Lovastatin, methyl-10H-3a,10a-epidithio-pyrazinol[1,2 .alpha.]indole-1,4-dione, 4-Hydroxy-3-nitrophenylacetyl-Leu-Leu-Leu-vinyl 426104 .alpha.-Meth-yl-sulfone clasto-Lactacystin .beta.-Lactone, 4-Hydroxy-5-iodo-3-nitrophenylacetyl-Leu-Leu-□-Methyl-omuralide Leu-vinylsulfone, Ac-hFLFL-epoxide, Mevinolin, Aclacinomycin A, Streptomyces galilaeus, MG 101, Aclarubicin, MG-115, ACM, MG-132, AdaAhx3L3VS, MG-132 in Solution, AdaK(Bio)AhX3L3VS, MG-262, AdaLys(Bio)Ahx3L3, MK-803, Adamantane-acetyl-(6-aminohexanoyl), NIP-L3VS 3-(leucunyl)3-vinyl-(methyl)-sulfone, ALLM, NLVS, ALLN, NP-L3VS, Calpain Inhibitor I, NP-LLL-VS, Calpain Inhibitor II, Omuralide, Carbobenzoxy-L-leucyl-L-leucyl-L-leucinal, PR-11, Carbobenzoxy-L-leucyl-L-leucyl-L-norvalinal, PR-39, Gliotoxin, Gladiocladium fimbriatum, Isovaleryl-L-tyrosyl-L-valyl-DL-tyrosinal, Lactacystin, Synthetic, clasto-Lactacystin β-Lactone, Z-LL-Nva-CHO, Ubiquitin Aldehyde, YU101, Ro106-9920, Z-GPFL-CHO, Ro106-9920 Tyropeptin A, and the like.

In one embodiment, the invention provides the compositions described herein above in the methods provided herein. Accordingly and in another embodiment, provided herein is a composition for modulating the Nrf2/ARE pathway in a subject, comprising flaxseed lignan complex metabolites, whereby Flaxseed lignans ED/EL are shown to act directly (or indirectly) on nrf2, thus, inducing its translocation to the nucleus and activation of the ARE-regulated transcription. In Aim 1, we will investigate if nrf2 is required and/or sufficient to induce endogenous AOE enhancement. In another embodiment, the flaxseed lignans used in the compositions and methods provided herein, are enterodiol, enterolactone, seciosolariciresinol diglucoside (SDG), or a combination thereof.

In another embodiment, any embodiment of a composition described in the methods provided herein, is encompassed in the compositions of the invention.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Figure 2:
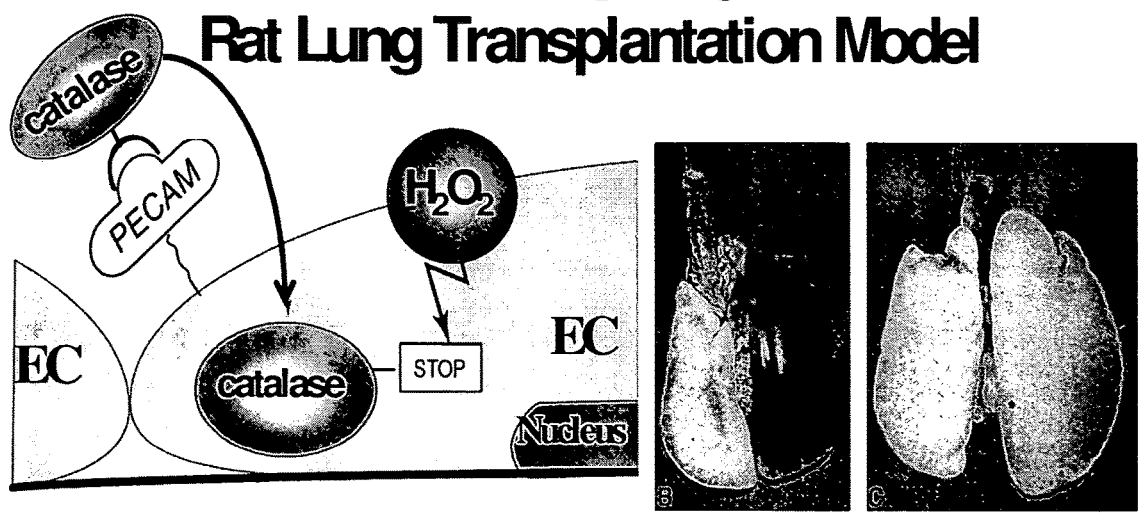
FIG. 2: shows a) schematic representation of ROS detoxification by immunotargeting of catalase in the vessel lumen; b) severe injury of left lung transplant after cold ischemia; and c) protection by anti-PECAM/catalase; taken from: Kozower, B. D., M. Christofidou-Solomidou, T. D. Sweitzer, S. Muro, D. G. Buerk, C. C. Solomides, S. M. Albelda, G. A. Patterson, and V. R. Muzykantov. 2003. Immunotargeting of catalase to the pulmonary endothelium alleviates oxidative stress and reduces acute lung transplantation injury. *Nat Biotechnol* 21:392-398.

Example 1: Delivery of Endothelial Antioxidant Enzymes can Prevent Lung Transplant Injury Using a rodent model of lung transplantation, targeted antioxidant enzyme delivery to the pulmonary endothelium, were investigated and antioxidant treatment of the pulmonary endothelium by vascular immunotargeting of catalase were shown to alleviates oxidative stress and reduces acute lung transplantation injury—see FIG. 2. This strategy, has established that alleviation of endothelial oxidative stress is sufficient to confer significant tissue protection in IRI.

These findings validate the therapeutic potential of boosting vascular antioxidant defense as a novel strategy to reduce tissue injury with lung transplantation. Potential applications of this strategy include improving the outcome of clinical lung transplantation and a wide variety of endothelial disorders. Provided herein is a non-toxic, safe dietary agents that act by boosting the intracellular, endogenous antioxidant defense and prevent endothelial ROS generation in the lung.

Example 2: Flaxseed and its By-Products as Bioactive, Therapeutic Dietary Supplements Flax is an annual plant that thrives in deep moist soils rich in sand, silt, and clay. The seeds in the flax plant are filled with flaxseed oil, sometimes called linseed oil. Flaxseeds are known as *Linum usitatissimum* with the species name meaning "most useful". The flax plant originated in Mesopotamia and first records of the culinary use of flaxseeds is from times of ancient Greece. Flaxseed was first planted in the US with the arrival of the early colonists in North. In the 17th century, flax was first introduced and planted in Canada, the country that is currently the major producer.

Figure 3:
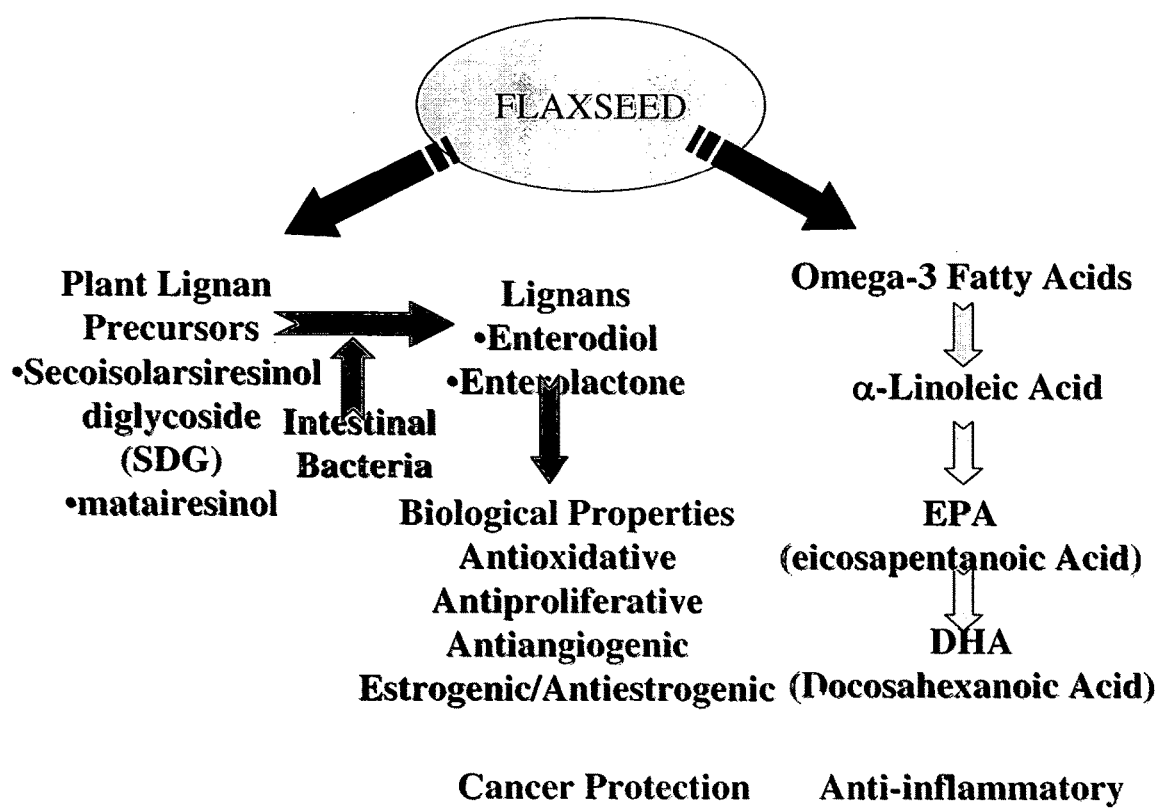
FIG. 3: shows a schematic of the various components of flaxseed; Lignans and Omega-3 Fatty acids.

Flax products are made from the seeds found inside the fruits. The seeds contain a fatty oil called alpha-linolenic acid (ALA), an essential fatty acid and linoleic acid (see FIG. 3). Essential fatty acids (EFA's) are the primary nutritional component of flax seed. The two key EFA's are Linoleic and linolenic. Flax seed oil has a high amount of these two EFA's, and therein lies the reason for the oils' demand. ALA is a precursor of eicosapentaenoic acid (EPA) and docosahexaenoic acid (DHA), which belong to omega-3 fatty acids. While EPA and DHA are found primarily in fish, ALA is mostly found in flaxseed oil and other vegetable oils. Omega-3 fatty acids help reduce inflammation and most omega-6 fatty acids tend to promote inflammation. Studies suggest that flaxseed oil and other omega-3 fatty acids may be helpful in treating a variety of inflammatory conditions, such autoimmune diseases. For example, systemic lupus erythematosus (SLE).

Dietary flaxseed has provided significant benefits in animal models of lupus nephritis and in patients with this condition, and carbon tetrachloride-induced hepatic injury. The evidence for the use of flaxseed oil is strongest for heart disease and problems that contribute to heart disease. Flaxseed (as opposed to flaxseed oil) is also a good source of phytoestrogens.

In addition to omega-3 fatty acids, flaxseed products also contain potentially therapeutic chemicals called lignans. Lignans are widely occurring plant compounds and are closely related to lignin, which forms the woody component of trees and other plants. The lignans are characterized by their dimeric composition from cinnamic acids, and they are attracting increasing attention as a result of their pharmacological properties. Lignans are believed to have direct antioxidant properties and can inhibit lipid peroxidation in tissues such as the brain.

Figure 4:
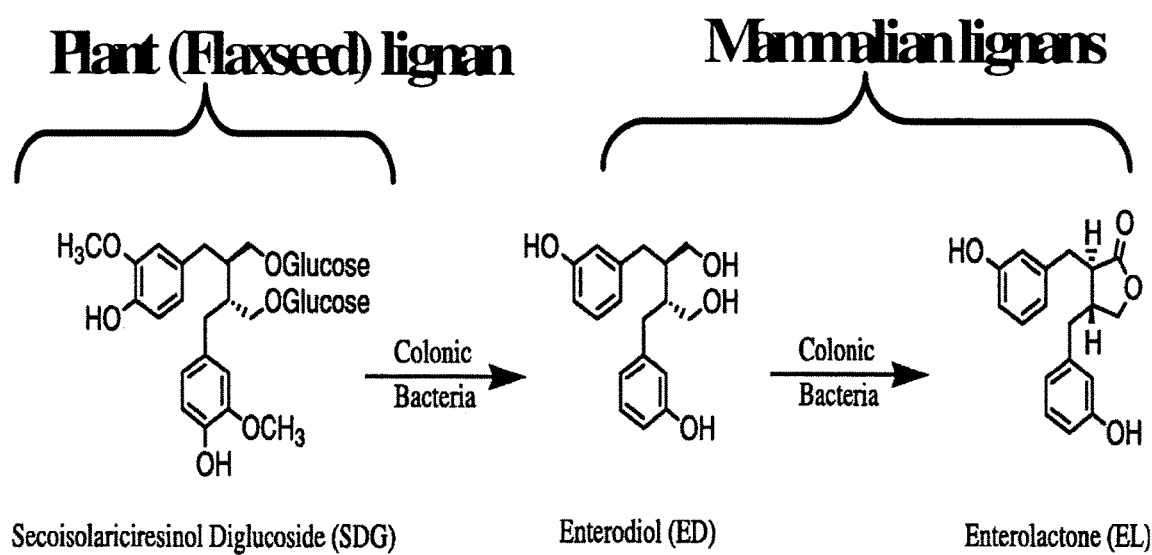
FIG. 4: shows how Secoisolariciresinol diglucoside (SDG), an antioxidant isolated from flaxseed, is metabolized in the human intestine to enterodiol (ED), and enterolactone (EL).

Secoisolariciresinol diglucoside (SDG), an antioxidant isolated from flaxseed, is metabolized in the human intestine to enterodiol (ED), and enterolactone (EL) (see FIG. 4). It will be important for future experiments to note that SDG is not directly taken up by cells, unlike ED and EL. The ex vivo antioxidant activities of these three lignans (SDG, EL and ED) were shown by specifically inhibiting linoleic acid lipid peroxidation, indicating direct hydroxyl radical scavenging activity. In addition, due to their ability to inhibit platelet activating factor (PAF), lignans may exert antioxidant activity by inhibiting ROS production by white blood cells. When tested therapeutically in streptozotosin-induced Diabetes mellitus, a condition associated with both ROS generation and PMN activation, SDG-treated animals resulted in prevention of diabetes, decrease in serum and pancreatic lipid peroxidation as well as a decrease in WBC-derived ROS. In addition, the antioxidant reserve of the pancreas was significantly increased. It has been shown that dietary flaxseed supplementation, decreased carbon tetrachloride-induced oxidant stress and lipid peroxidation levels in blood and red blood cell membranes in rats.

Example 3: Lignans Modulate the Production of Antioxidant Enzymes (AOEs)

In addition to their direct antioxidant activities (described in the examples above), some lignans have also been shown to upregulate endogenous antioxidant defenses such as the Phase I and Phase II enzymes which are first lines of defense against xenobiotics and more specifically act against dietary and environmental carcinogens that enter the body. The Phase I enzymes identify pre-carcinogenic compounds (xenobiotics) and make them more reactive, more water-soluble and easier for the body to dispose of (often via the action of Phase II enzymes). Phase I enzymes consist of CYPp450 family of cytochromes. Proteins belonging to this class of enzyme catalyze reactions resulting in the addition of functional groups and reactive centers e.g. SH, OH, —NH2 and —COOH groups to their substrates. Enzymes involved in the Phase II or the detoxification process e.g. Glutathione —S— transferase, and the N-acetyl transferases are responsible for the deactivation of radicals and electrophiles known to intervene in normal cellular processes, prior to their excretion.

The lignan sesamin (derived from sesame seeds), has been shown to stimulate the production of glutathione S— transferase (GST). GST is a "Phase II" detoxifying enzyme that catalyzes the reaction of glutathione with electrophiles to form compounds that are less toxic, more water-soluble, and can be excreted easily. The in vivo antioxidant action of a lignan-enriched extract from fruits was further evidenced by enhancement in hepatic mitochondrial glutathione antioxidant status, as evidenced by increases in reduced glutathione levels and increased activities of glutathione reductase (GR), glutathione peroxidase (GPx), as well as glutathione S-transferases. Sesame-derived lignans (sesamin and episesamin) were shown to decrease exercise-dependent lipid peroxidation in mice and enhance the enzymatic activity of both GST and GPx thus conferring protection. Yu et al [Ikeda, T., Y. Nishijima, H. Shibata, Y. Kiso, K. Ohnuki, T. Fushiki, and T. Moritani. 2003. Protective effect of sesamin administration on exercise-induced lipid peroxidation. *Int J Sports Med* 24:530-534.], isolated eleven lignans from the bark of a plant which were shown to have hepatoprotective properties by significantly preserving the levels and the activities of glutathione, and the AOEs, superoxide dismutase, glutathione peroxidase and catalase as well as ameliorated lipid peroxidation as demonstrated by a reduction of MDA production. Glutathione, superoxide dismutase (SOD) and glutathione peroxidase all play important roles in the cellular defense against oxidative stress. Prasad and coworkers [Prasad, K., S. V. Mantha, A. D. Muir, and N. D. Westcott. 1998. Reduction of hypercholesterolemic atherosclerosis by CDC-flaxseed with very low alpha-linolenic acid. *Atherosclerosis* 136:367-375, Pattanaik, U., and K.

Prasad. 1998. Oxygen Free Radicals and Endotoxic Shock: Effect of Flaxseed. *J Cardiovasc Pharmacol Ther* 3:305-318], investigated cardiac dysfunction and tissue injury during endotoxemia in dogs placed on flaxseed diets, a condition related to increased levels of oxygen free radicals. They measured, among other, antioxidant enzyme activity (superoxide dismutase, catalase, glutathione peroxidase), as well as cardiac malondialdehyde (MDA) concentration which is a lipid peroxidation product. They concluded that pretreatment up to 6 days with flaxseed attenuated the endotoxin-induced cardiac dysfunction and cellular damage. Example 1, showed for the first time that dietary flaxseed and more specifically flaxseed lignans, have potent anti-inflammatory and antioxidant effects in lung tissues in murine models of oxidative acute lung injury.

Although the antioxidant properties of flaxseed have been recognized, the molecular mechanism(s) of antioxidant protection by flaxseed or its individual bioactive ingredients lignans has not been carefully explored.

Example 4: The Nrf2/ARE Signaling Pathway

Figure 5:
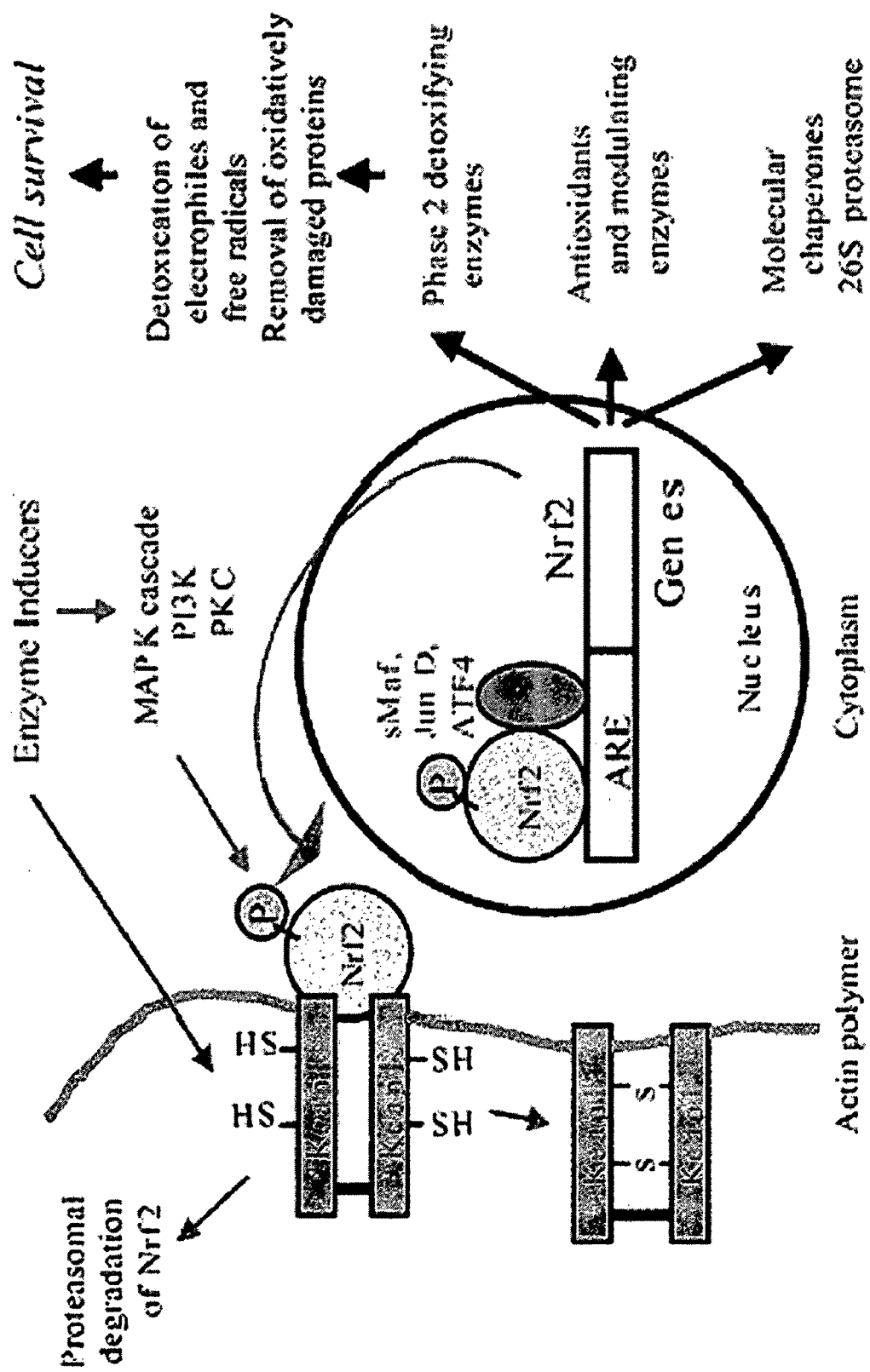
FIG. 5: shows a schematic of the Nrf2/ARE signaling pathway taken from Wakabayashi, N., Itoh, K., Wakabayashi, J., Motohashi, H., Noda, S., Takahashi, S., Imakado, S., Kotsuji, T., Otsuka, F., Roop, D. R., Harada, T., Engel, J. D., and Yamamoto, M. (2003). Keap1-null mutation leads to postnatal lethality due to constitutive Nrf2 activation. Nat Genet 35, 238-245.

Many endogenous antioxidant enzymes such as hemeoxygenase I (including most of the Phase II enzymes such as GST, NQO-1, acetyltransferase, sulfotransferase) are regulated by a "master" antioxidant transcription factor called Nrf2, in much the same way that many inflammatory proteins and cytokines are regulated by the master transcription factor NF-κB (see FIG. 5). The transcription factor Nrf2 binds to and activates a specific "antioxidant response element" (ARE) in the promoter region of many detoxifying and anti-oxidant enzyme genes. Its regulation is similar to that of NF-κB. Under homeostatic conditions Nrf2 is bound by a protein called Keap1 that keeps the complex in the cytoplasm; Keap1 thus being a negative regulator of Nrf2. Electrophiles and reactive oxygen species liberate Nrf2 from Keap1 and induce the translocation and accumulation of Nrf2 in the nucleus (FIG. 5). Once in the nucleus, binding of nrf2 to the antioxidant response element (ARE) drives the induction of a gene groups that may facilitate the detoxification of carcinogens, enhance the reducing potential against electrophiles and free radicals, and elevate cellular capacity for repair/removal of oxidatively damaged proteins-see FIG. 5.

Flaxseed lignans are shown to act directly (or indirectly) on nrf2, thus, inducing its translocation to the nucleus and activation of the ARE-regulated transcription. In Aim 1, we will investigate if nrf2 is required and/or sufficient to induce endogenous AOE enhancement.

Example 5: Flaxseed Supplementation Ameliorates Inflammation and Acute Lung Injury (ALI)

Figure 6:
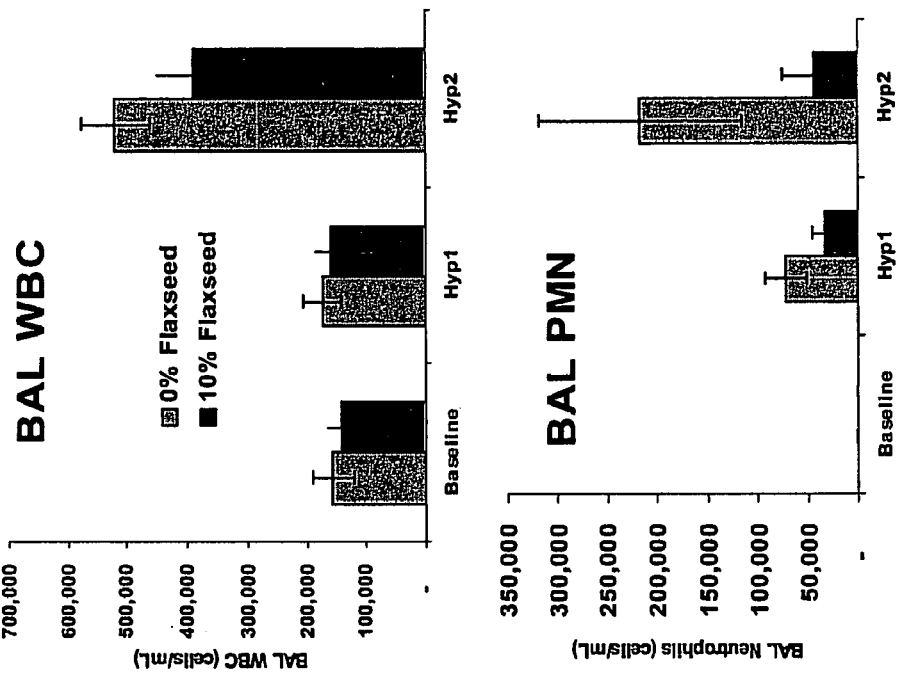
FIG. 6: shows the ability of whole grain dietary flaxseed (10%) to reduce lung injury in two models: acid aspiration-induced lung injury (24 hours), simulating oxidative lung injury resulting from aspiration of gastric contents, and an acute model of hyperoxia-induced ALI (80% O2 for 6 days).
Figure 6:
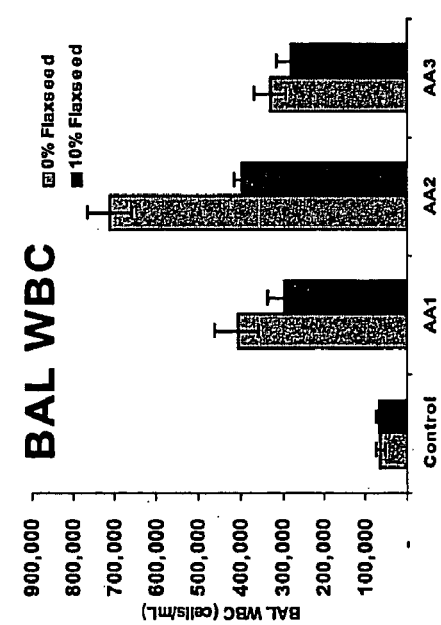
Figure 7:
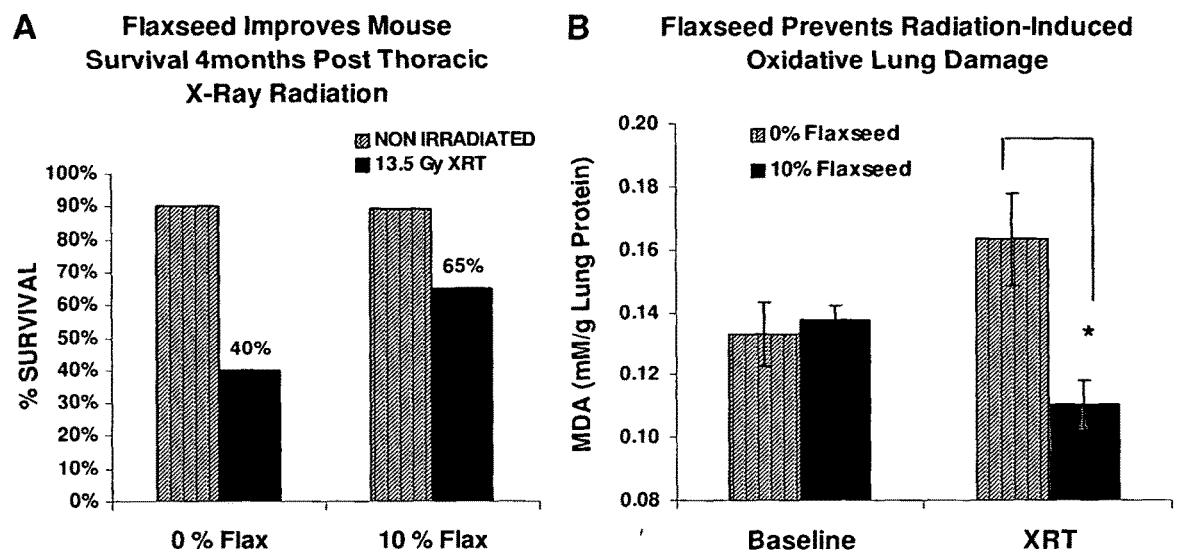
FIG. 7: shows a) three weeks of dietary flaxseed supplementation prior to the time of thoracic irradiation, leads to significantly increased mouse survival as compared to irradiated mice fed a standard, control diet; and b) Mouse weight, reflecting the animals' overall health and tolerability of the diet (3 weeks pre- and 4 months post-XRT), indicated that flaxseed-supplemented mice had gained weight and had an overall better health profile than control mice.

The ability of flaxseed to reduce lung injury was tested in two models: acid aspiration-induced lung injury (24 hours), simulating oxidative lung injury resulting from aspiration of gastric contents, and an acute model of hyperoxia-induced ALI (80% O2 for 6 days). Mice were placed on a 10% flaxseed diet for 3 weeks (to ensure a steady state), versus a specially designed isocaloric basic diet. Results are shown in FIG. 6. Experiments were repeated twice for hyperoxia (Hyp1 and Hyp2) and three times for Acid Aspiration (AA1, AA2 and AA3). Bronchoalveolar lavage (BAL) was evaluated for A) white blood cells (WBC) and b) neutrophils (PMN), 24 h post intratracheal challenge of hydrochloric acid, or after 6 d of hyperoxia. Following hyperoxia and acid aspiration, FS-supplemented mice had a significant decrease in BAL neutrophils while overall alveolar WBC influx tended to be lower. In summary, dietary FS decreased lung inflammation and injury in models of ALI, suggesting a protective role against pro-oxidant-induced ALI in vivo.

Example 6: Dietary Whole Grain Flaxseed (10%) is Highly Effective in a Murine Orthotopic Model of Bronchogenic Adenocarcinoma of the Lung A transgenic mouse was used, which allows regulated expression of one copy of a mutated Kras gene. The protein from the mutated gene is normally not expressed because the coding region is preceded by stop codon. However, this stop codon is flanked by two lox recombination sites. Thus, when the animals are injected intratracheally with an adenovirus expressing cre recombinase (Ad.Cre), the epithelial cells that take up the transgene excise the stop codon and begin to express the mutated Kras. This oncogene then induces the formation of malignant lung lesions. The lesions start as adenomatous hyperplasia, but soon progress to frank adenocarcinomas as shown by the histological evaluation. Depending on the dose of Ad.Cre, the number lesions and the extent of tumor can be controlled. In this model, using $10^9$ pfu of Ad.Cre, detectable tumors are obtained at 14-21 days and death by about 45 days.

The Kras model of lung bronchoalveolar carcinoma was used to test whether dietary flaxseed blocked tumor growth. Mice were injected intratracheally with 5×109 Ad.Cre virus particles to initiate tumor formation and diet was initiated (0% vs. 10% Flaxseed) on the same day (n=20 per diet). Three (3) mice from each diet (Mouse 1-3 from 10% Flaxseed and mouse 21-23 from the 0% flaxseed diet) were sacrificed a month post tumor initiation for histopathological assessment. Hisatological evaluation indicated a clear protection by the flaxseed diet which was confirmed by measurements of tumor area using image analysis software (57% tumor vs. 13% for 0% vs. 10% flax, respectively). See FIG. 26.

These data provide clear evidence that flaxseed is protective in in lung cancer. No toxicity was noted at the dose tested.

Figure 8:
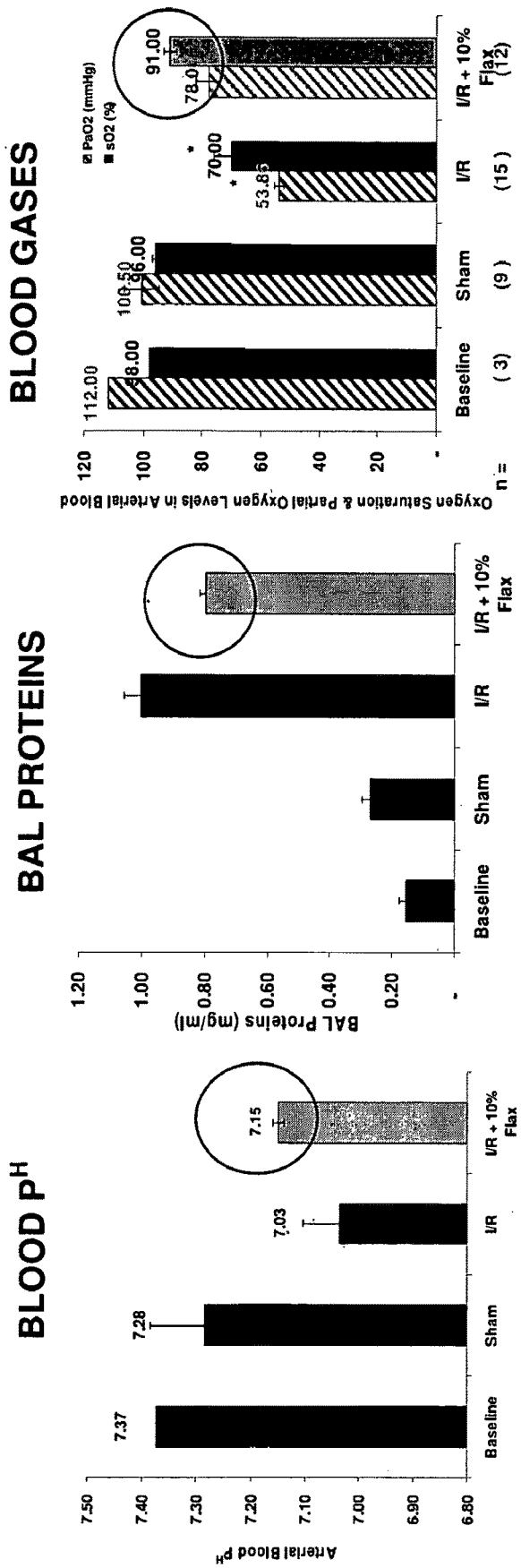
FIG. 8: shows the effects of high FS diet in a murine model of ALI induced by ischemia/reperfusion (I/R). Sham animals (undergoing thoracotomy, but not I/R) were used as controls. I/R injury was evaluated using five parameters (FIG. 8-10): (1) physiologic arterial blood gases (ABG), (2) morphologic (histology) (3) biologic (bronchoalveolar lavage, BAL), (4) immunohistochemical and (5) biochemical (Malondialdehyde detection-MDA assay for lipid peroxidation).
Figure 22:
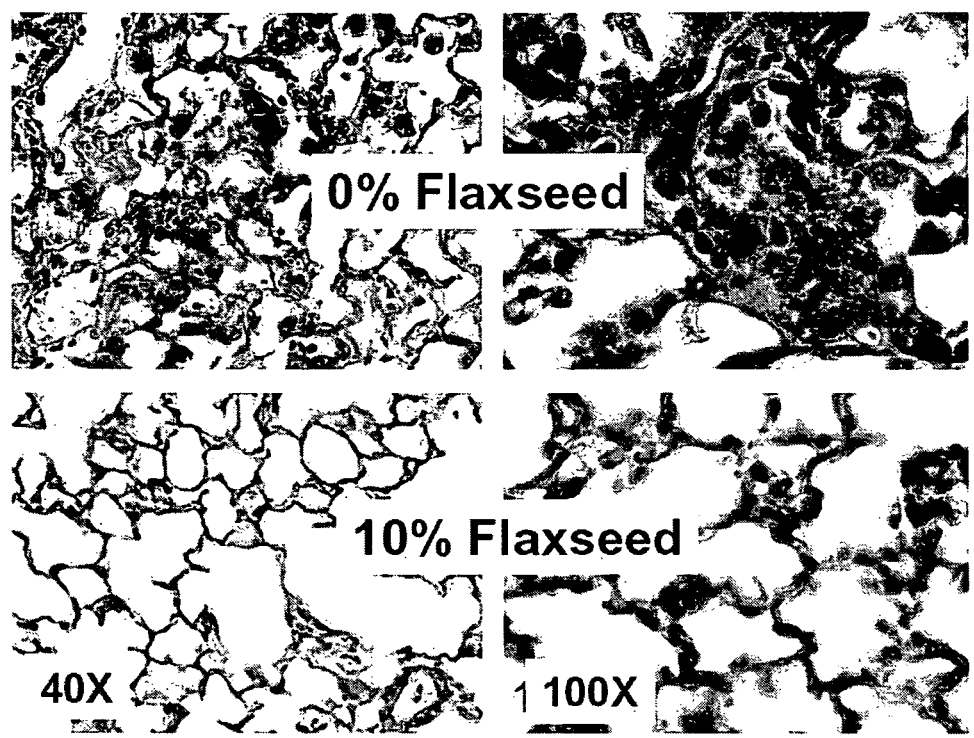
FIG. 22: shows how whole grain dietary flaxseed (10%) prevents lung fibrosis resulting from Xray radiation treatment (XRT) of mouse lung. Blue color indicates collagen deposition (resulting in lung stiffness and ultimately, death). Less collagen is seen with Flaxseed supplementation (bottom panels).
Figure 23:
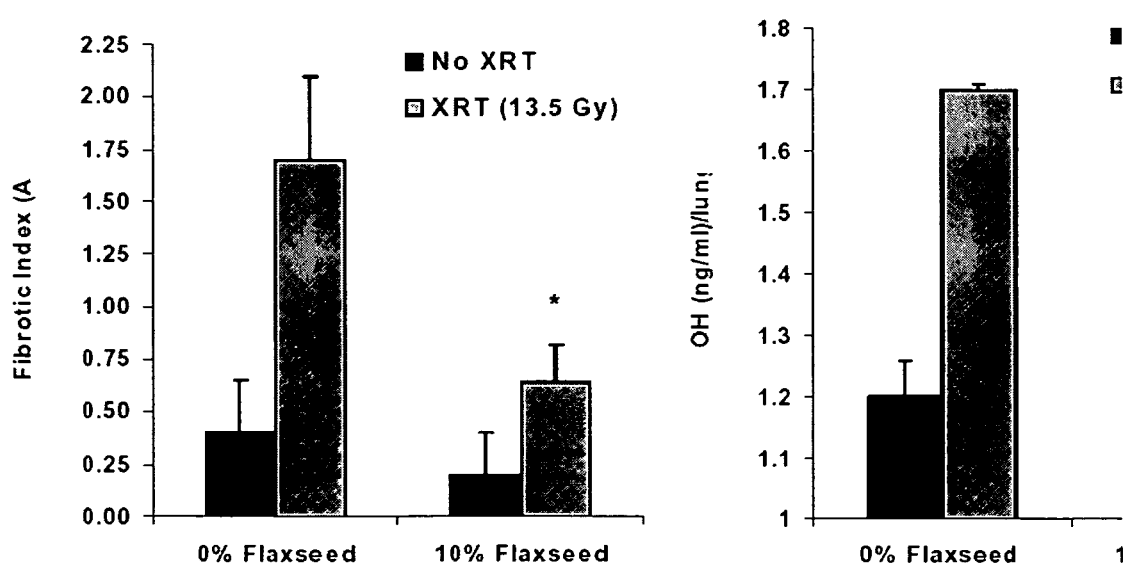
FIG. 23: shows semiquantitative (left) and quantitative (right) assessment of lung fibrosis taken from histological assessment of lung sections or whole lung homogenates respectively.
Figure 24:
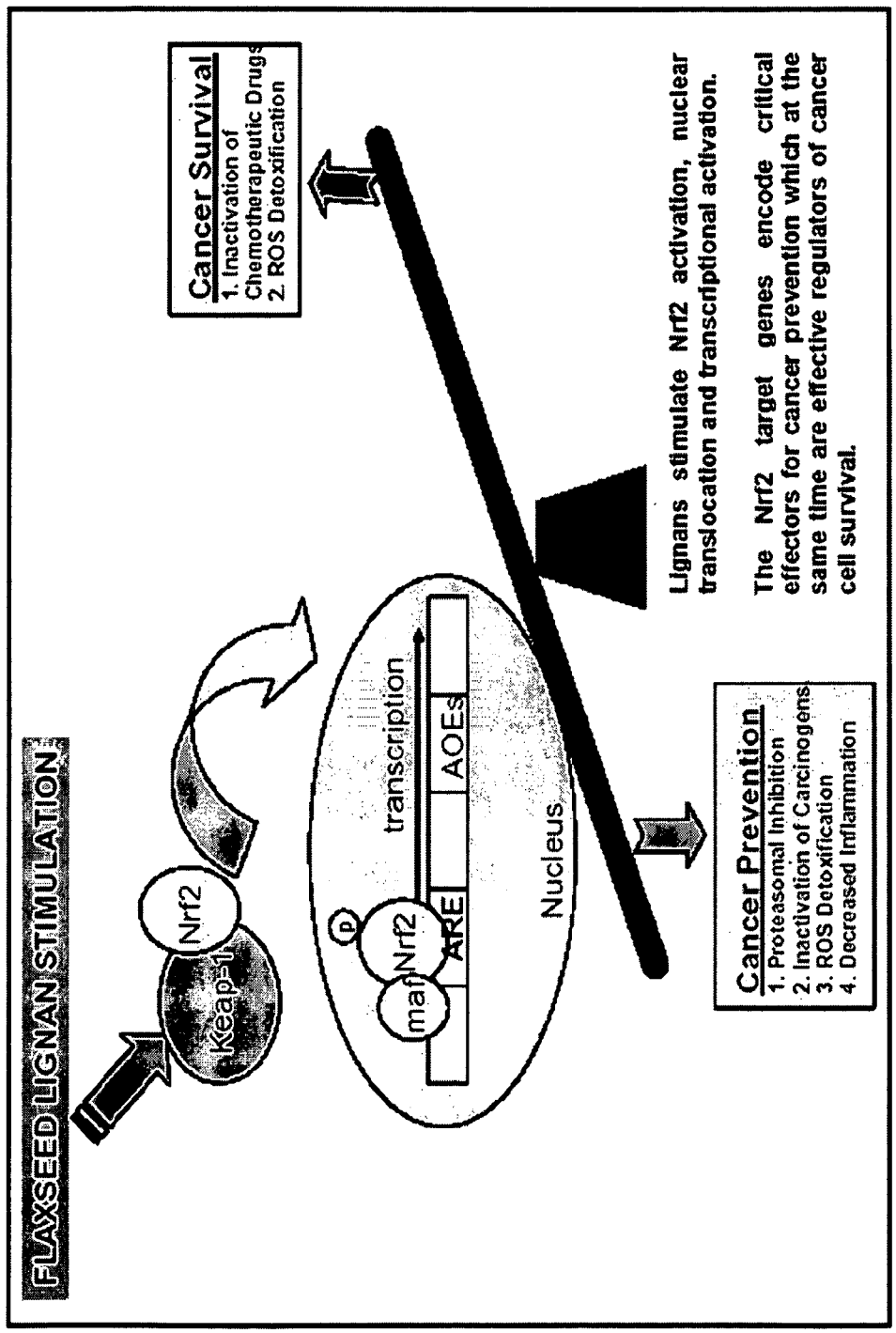
FIG. 24: shows a schematic of anticarcinogenic effects of lignans: Flaxseed, via the action of the lignans, modulates the tumor microenvironment and thus affects tumor growth and metastasis.

Example 7: Dietary Flaxseed Alleviates Thoracic X-Ray Radiation (XRT)-Induced Oxidative Lung Injury and Improves Survival in a Murine Model Another model of lung ROS injury is lung irradiation. The effectiveness of radiotherapy for intrathoracic malignancies is greatly limited by the radiation tolerance of normal structures. In particular, the lung is especially sensitive to the damaging effects of irradiation. It is now accepted that DNA damage is the primary mechanism by which radiation causes cell injury and death and that most of this damage to DNA is produced indirectly, by ionizing other molecules (e.g. water) to produce free radicals that then react with the DNA. The radiohydrolysis of water molecules gives rise to extremely damaging ROS. Oxidative modification of proteins by formation of Nitrotyrosine and of lipids has been reported, although the molecular pathways from the oxidative tissue insult to late fibrosis are unclear. Lipid peroxides generated as a result of thoracic XRT, can undergo further decomposition to give products like malondialdehyde (MDA) that can be detected by sensitive assays. A 10% flaxseed-supplemented diet was evaluated in a mouse thoracic XRT model with respect to lipid peroxidation (MDA formation) over time: Three weeks of dietary flaxseed supplementation prior to the time of thoracic irradiation, led to significantly increased mouse survival as compared to irradiated mice fed a standard, control diet (FIG. 8A). Mouse weight, reflecting the animals' overall health and tolerability of the diet (3 weeks pre- and 4 months post-XRT), indicated that flaxseed-supplemented mice had gained weight and had an overall better health profile than control mice. A significantly decreased oxidative modification of irradiated lungs was observed 4 months post-radiation, as measured by MDA (FIG. 8B). FIG. 22 indicates histological evaluation of lung fibrosis and FIG. 25, quantitative analysis of lung collagen levels confirming findings that indicate a clear protective role of Flaxseed.

These data provide further evidence that dietary supplementation of flaxseed has therapeutic applications in ameliorating tissue oxidant stress. In addition, prolonged supplementation (4 months) is well tolerated and improves overall animal health.

Example 8: Flaxseed Supplementation Ameliorates Lung Ischemia Reperfusion Injury in Mice Next whether flaxseed diets in a mouse model that are directly induced lung ischemia-reperfusion injury, was tested in a manner more similar to what might be seen in transplantation. The effects of high FS diet was tested in a murine model of ALI induced by ischemia/reperfusion (I/R). Mice were thus anesthetized; tracheostomy and mechanical ventilation was performed ($FIO_2$ 21%, TV 10 ml/kg, RR 130/min). Thoracotomy was performed and the left pulmonary hilum clamped for 60 minutes. The clamp was then removed and reperfusion allowed for an additional 60 minutes. Sham animals (undergoing thoracotomy, but not I/R) were used as controls. I/R injury was evaluated using five parameters (FIG. 8-10): (1) physiologic arterial blood gases (ABG), (2) morphologic (histology) (3) biologic (bronchoalveolar lavage, BAL), (4) immunohistochemical and (5) biochemical (Malondialdehyde detection-MDA assay for lipid peroxidation).

Mice were fed specially formulated FS diets (0% or 10%) for several weeks and were then subjected to IRI. Sham animals had normal arterial $PaO_2$, arterial saturation, BAL protein (FIG. 8) and histology (FIG. 9) compared to untreated mice. Mice fed 0% FS had a significant decrease in arterial $PaO_2$ and saturation compared to sham (54±2 vs 101±11 $PaO_2$; 70±4 vs 95±2 saturation), a significant increase in BAL protein (1.0±0.05 vs 0.27±0.03) and marked perivascular and alveolar edema, intra-alveolar hemorrhage and WBC accumulation compared to sham.

Figure 10:
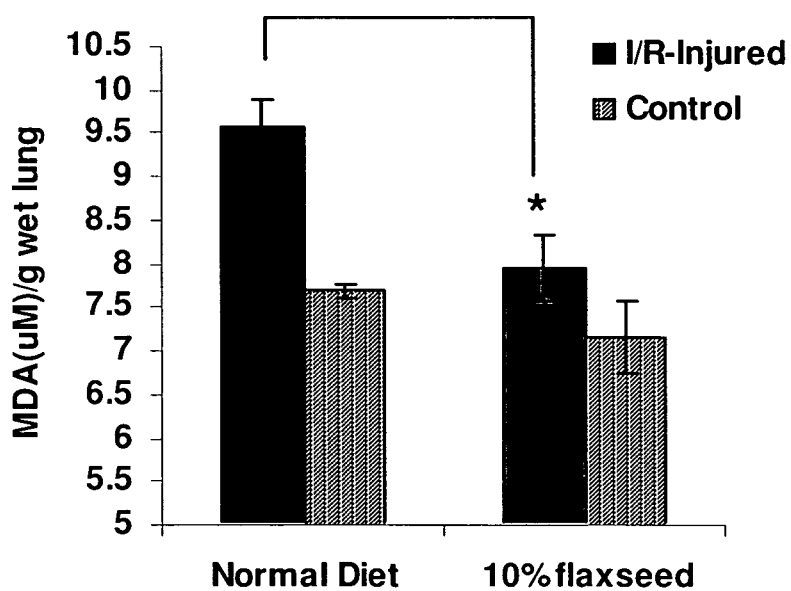
FIG. 10: shows directly measured MDA levels.

Remarkably, mice fed 10% FS had significant improvement in arterial $PaO_2$ and saturation compared to 0% FS (81±4 vs 54±2 $PaO_2$; 91±2 vs 70±4 saturation), a significant decrease in lung BAL protein (0.8±0.04 vs 1.0±0.05) (FIG. 10) and no histological features of I/R injury compared to 0% FS. (n>6, all groups blinded) (FIG. 10—H&E histology).

Figure 9:
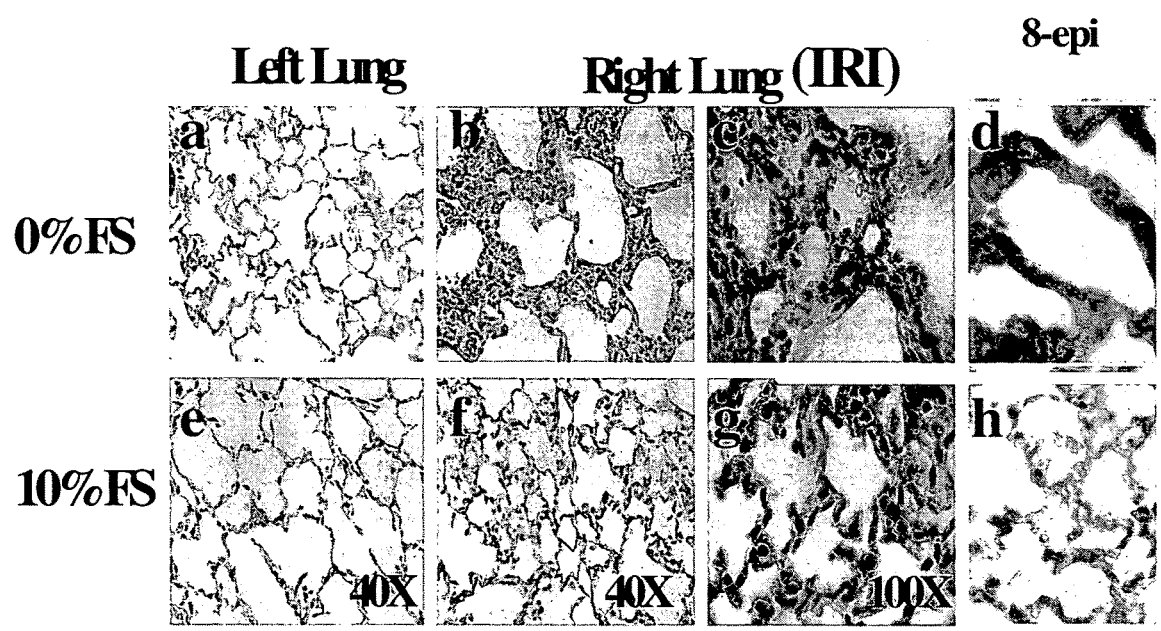
FIG. 9: shows the histological effects of high FS diet in a murine model of ALI induced by ischemia/reperfusion (I/R). Sham animals (undergoing thoracotomy, but not I/R) were used as controls.

To evaluate the extent of oxidative injury and identify products of tissue oxidation, IRI lungs were stained with an antibody directed against $iPF_{2\alpha}$-III (an $F_2$ isoprostane reflecting lipid peroxidation—(anti-8epi antibody). Lipid peroxidation was significantly blunted in Flaxseed-fed animals following IRI as shown by the decreased blue staining (FIG. 9-h vs. d). MDA levels were measured directly as shown in FIG. 10. The flaxseed diet significantly reduced the levels of MDA after IRI.

This data shows that dietary FS is clearly protective against I/R injury in a murine model of ALI, as demonstrated by an improvement in physiologic, histological and biologic parameters.

Example 9: Dietary Flaxseed Protects from Lung Transplantation-Related Acute Lung Injury in a Rat Model of Orthotopic Lung Transplantation A rat model of rat lung transplantation was recently developed. As a preliminary test of the hypothesis that flaxseed diets could ameliorate lung transplant induced IRI, some very preliminary studies were conducted in three rats. Flaxseed diets were fed to both donor and recipient rats (2 weeks on diet) prior to lung transplantation. Eighteen hours post-transplantation, hemodynamic parameters were determined and a histopathological examination of the lung was performed. Flaxseed-treated rats showed decreased lung inflammation and interstitial edema (FIG. 11C) associated with the procedure as compared to rats fed a normal chow (FIG. 11B) while FIG. 11A is an untreated control lung. In addition, peak lung pressures were significantly improved in flaxseed-fed rats (FIG. 12).

This data shows that the flaxseed/transplant hypothesis is valid.

Figure 13:
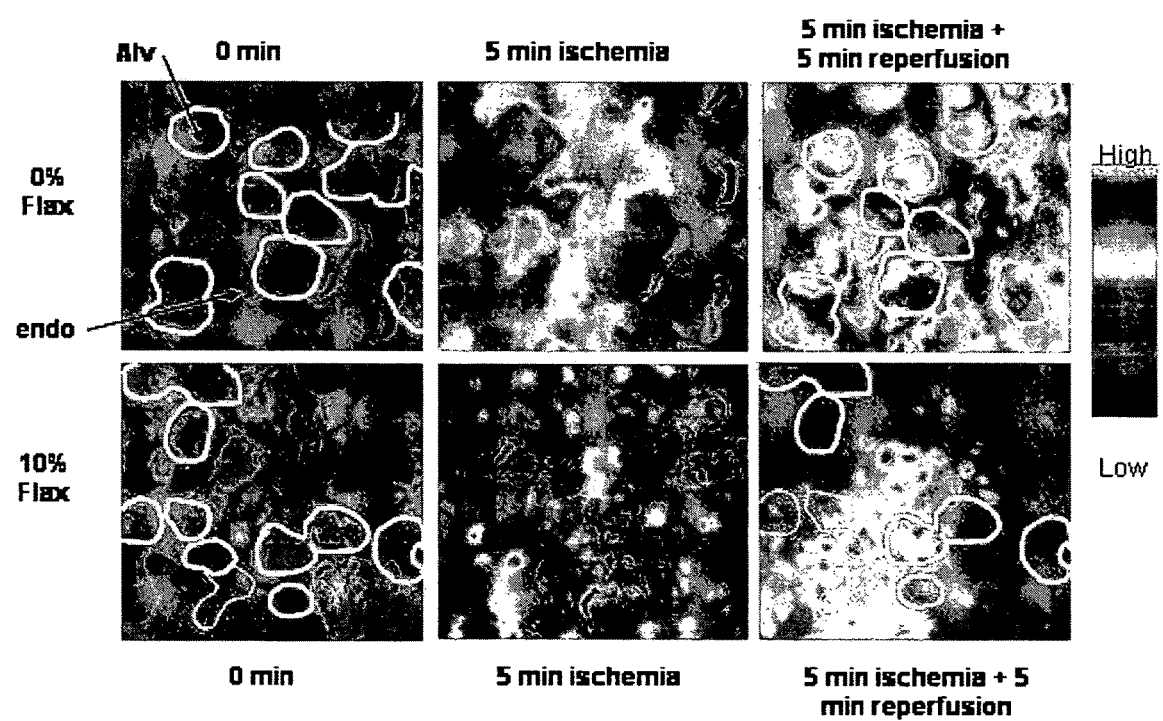
FIG. 13: shows in-vivo imaging of the effect of a flaxseed diet on generation of ROS in EC after IR.

Example 10: Dietary Flaxseed Inhibits Endothelial ROS Generation in an Ex Vivo Model of Lung Ischemia/Reperfusion The data presented above convincingly show that flaxseed diets reduce lung injury and reduce markers of oxidative injury, such as MDA levels, however these systems do not allow us to actually visualize ROS levels. To accomplish this, a system developed at PENN in was used, in which lung ischemia reperfusion is studied in real time, in living mice, using confocal microscopy to visualize specific injected, circulating fluorescent dyes that can measure ROS levels or other interesting cellular parameters (ion flows). Using this system, it was determined that quickly after flow is re-established in an ischemia reperfusion model, there is a marked rise in ROS production in lung endothelial cells. This is due to a mechanical transduction of the flow signal that first involves endothelial cell (EC) membrane depolarization mediated by an EC ATP-sensitive potassium ($K_{ATP}$) channel which then leads to assembly and activation of the NADPH oxidase complex in the EC membrane that produces high levels of endogenous ROS. Our collaborator, Dr. Chatterjee, used the in vivo imaging system to evaluate the effect of a flaxseed diet on generation of ROS in EC after IR—(FIG. 13).

Figure 14:
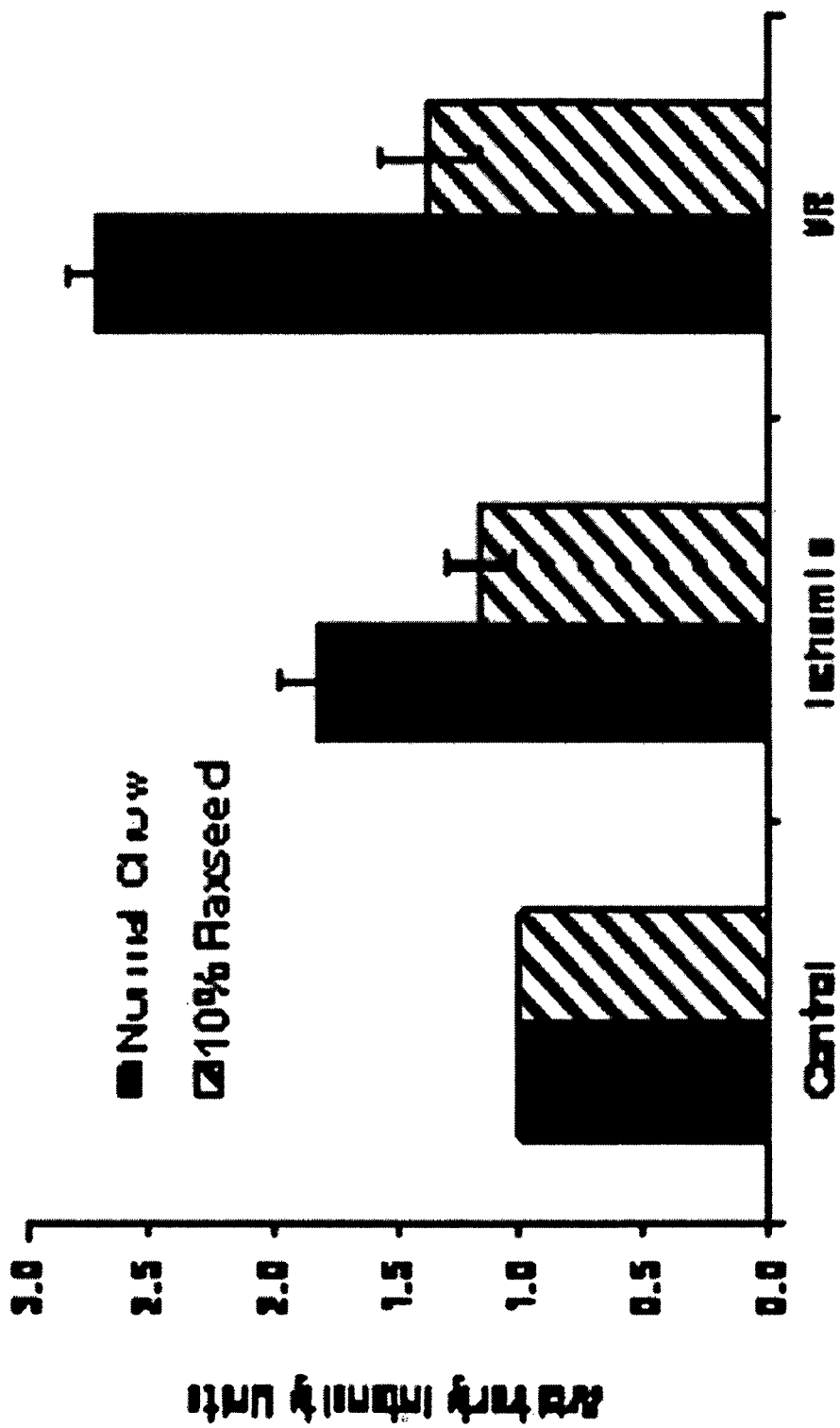
FIG. 14: shows increased intracellular ROS levels, as measured by 2',7'-dichlorodihydro fluorescein (DCF) taken by cells as measured by dye uptake. This was blunted in the Flax-fed animals.

Isolated perfused mouse lungs were taken from flaxseed-fed (3 weeks on 10% diet) or control mice and labeled with 2',7'-dichlorodihydro fluorescein (DCF). This dye is taken up by cells and measures ROS levels. The lungs were imaged using the confocal scope (0 min). After global ischemia (5 minutes), lungs were re-imaged. A small increase in dye intensity [red color] was seen in subpleural endothelial cells (see graph for quantification-FIG. 14) indicating increased intracellular ROS levels, but this was blunted in the Flax-fed animals. The lungs were then re-perfused for five minutes. At this time, a massive increase in ROS was seen in control animals (far left right panels) that was impressively blocked in the flax-fed animals. Semi quantitative assessment of at least 3 fields per lung (3 mice per diet) revealed a near 3-fold increase of fluorescence intensity with I/R in control diets and just 1.2-fold increase over baseline, with 10% dietary flaxseed supplementation.

This data clearly shows that the increased endothelial ROS generation induced by IRI is blunted by a flaxseed diet and illustrates our facility with a key experimental system we will use to dissect mechanisms.

Example 11: Flaxseed Upregulates Two Nrf2-Regulated Anti-Oxidant and Phase II Enzymes in Murine Lungs in a Dose-Dependent Manner One of the mechanistic hypotheses tested, is that flaxseed exerts some of its protective effects by upregulating Phase II enzymes in mouse lungs via in an Nrf-2-dependent manner.

Figure 15:
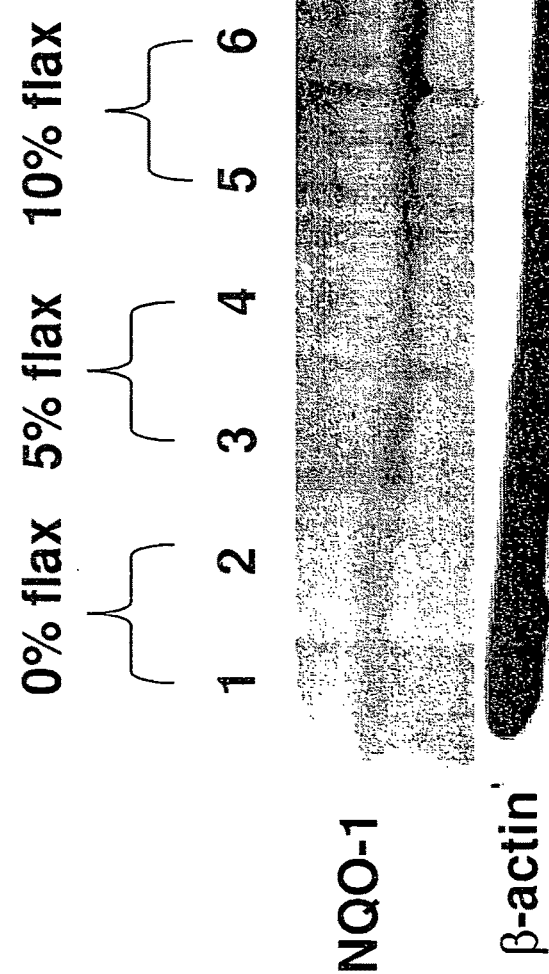
FIG. 15: shows dose dependent increases in quinone reductase (NQO-1) in mice fed a 0%, 5% and a 10% flax diet for 10 week.
Figure 16:
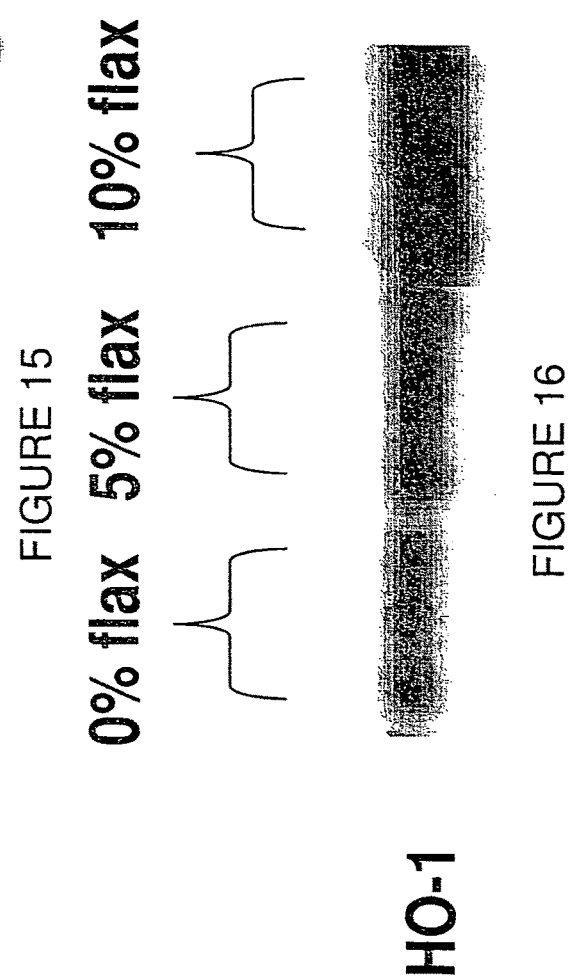
FIG. 16: shows dose dependent increases in the antioxidant enzyme HO-1 in mice fed a 0%, 5% and a 10% flax diet for 10 week.

First, mice were fed a 0%, 5% and a 10% flax diet for 10 weeks, lungs harvested, and processed for immunoblotting to measure levels of two Nrf2/ARE-dependent Phase II detoxification enzymes. These blots show dose dependent increases in quinone reductase (NQO-1) (FIG. 15) and the antioxidant enzyme HO-1 (FIG. 16) supporting the hypothesis that flaxseed acts via Nrf2-modulation of ARE-regulated genes.

This data is the first evidence that a flaxseed diet enhances AOEs in mouse tissues, and more specifically in mouse lungs.

Figure 17:
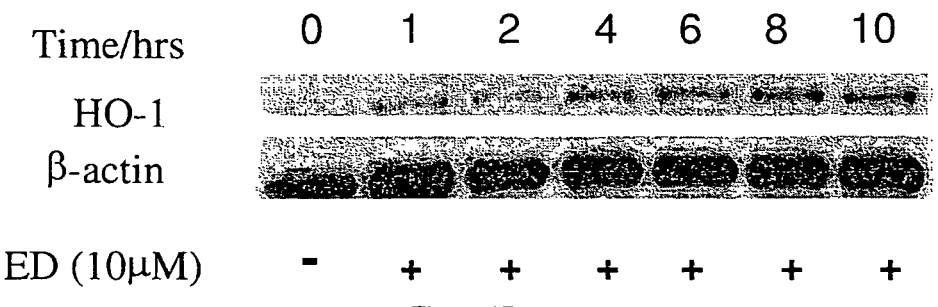
FIG. 17: shows addition of the flaxseed-derived lignan to the endothelial cells results in a robust, time-dependent induction of HO-1.

Example 12: Chemically Syntehsized Mammalian Flaxseed Lignans Upregulate Nrf2-Regulated Antioxidant Enzymes in Pulmonary Microvascular Endothelial Cells In Vitro For mechanistic studies, there is a need to establish whether purified lignans (in appropriate, "pharmacologically achievable" concentrations) have similar effects in cell culture as lignan complex diets have in animals. HO-1 levels were thus evaluated by immunoblotting in primary cultures of pulmonary microvascular endothelial cells (PMVEC) isolated from mouse lungs. PMVEC were incubated with the lignan enterodiole (ED) in micromolar concentrations (10 $\mu$M) similar to that seen in mouse plasma levels. Cells were incubated with ED for 1,2,4,6,8 and 10 hours. Addition of the flaxseed-derived lignan to the endothelial cells resulted in a robust, time-dependent induction of HO-1 (FIG. 17). Similar findings were shown with the flaxseed lignan (EL).

Figure 18:
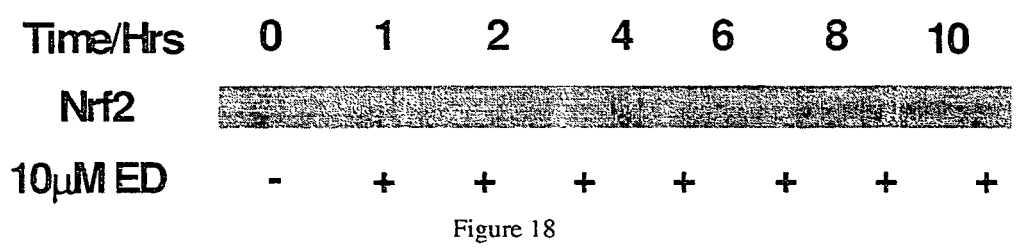
FIG. 18: shows that while very low basal levels of Nrf2 are present in control, untreated cells at all times, (first lane, control), lignans induced a time-dependent increase of nuclear_Nrf2 levels.

Treatment of unchallenged, primary cultures of isolated pulmonary microvascular endothelial cells with flaxseed lignan ED (10 $\mu$M) indicated that while very low basal levels of Nrf2 are present in control, untreated cells at all times, (first lane, control), lignans induced a time-dependent increase of nuclear Nrf2 levels (FIG. 18). Similar findings were shown with EL. Nrf2 was detected with our own rabbit polyclonal Antibody (Clone MCS-1a).

Example 13: Flaxseed Lignans Reduce Cell Death Induced by Oxidative Stress

Figure 19:
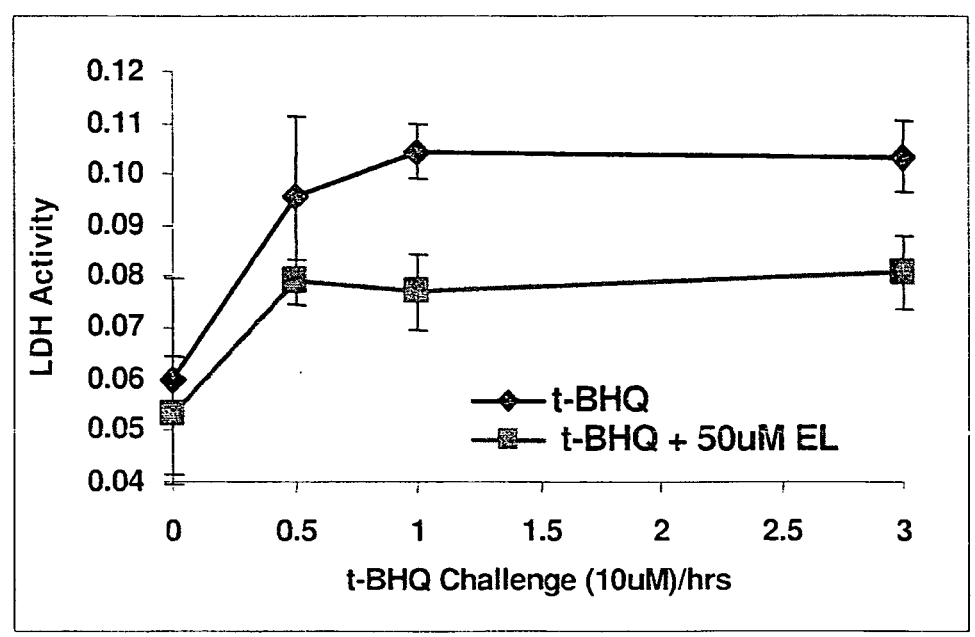
FIG. 19: shows that treatment of PMVEC with 10 □M of tBHQ leads to marked LDH release (indicating cell death) of PMVEC within 30-60 minutes. However, pretreatment of cells with 50□M of the chemically synthesized, commercially available lignan Enterolactone (EL) is sufficient to protect cells up to 50% from tert-butylhydroquinone (tBHQ)-induced cell death.
Figure 21:
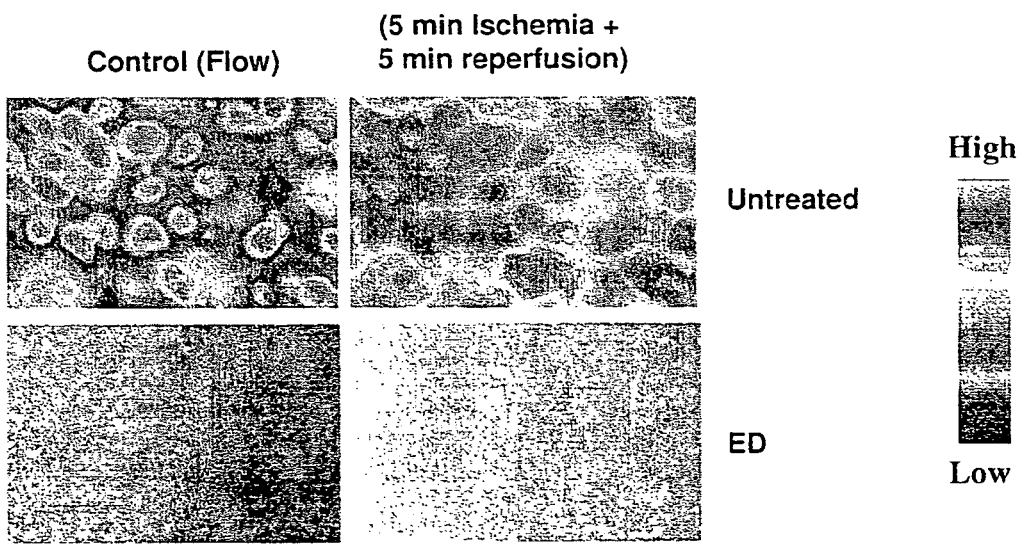
FIG. 21: shows a near complete abrogation of ROS generation by chemically synthesized, commercially available lignan-pre-treated EC, as evidenced from pseudocolor images of H2DCF uptake by the cells to monitor ROS generation.

Given the in vivo data hereinabove, showing protection of lungs from oxidative injury after flaxseed feeding, a confirmation of similar protection of cells in vitro was desired. Relatively high doses of the electrophile tert-butylhydroquinone (tBHQ) were used to oxidatively stress the cells. As shown in FIG. 21, treatment of PMVEC with 10 $\mu$M of tBHQ led to marked LDH release (indicating cell death) of PMVEC within 30-60 minutes. However, pretreatment of cells with 50 $\mu$M of the lignan Enterolactone (EL) was sufficient to protect cells up to 50% from tert-butylhydroquinone (tBHQ)-induced cell death (FIG. 19).

Figure 20:
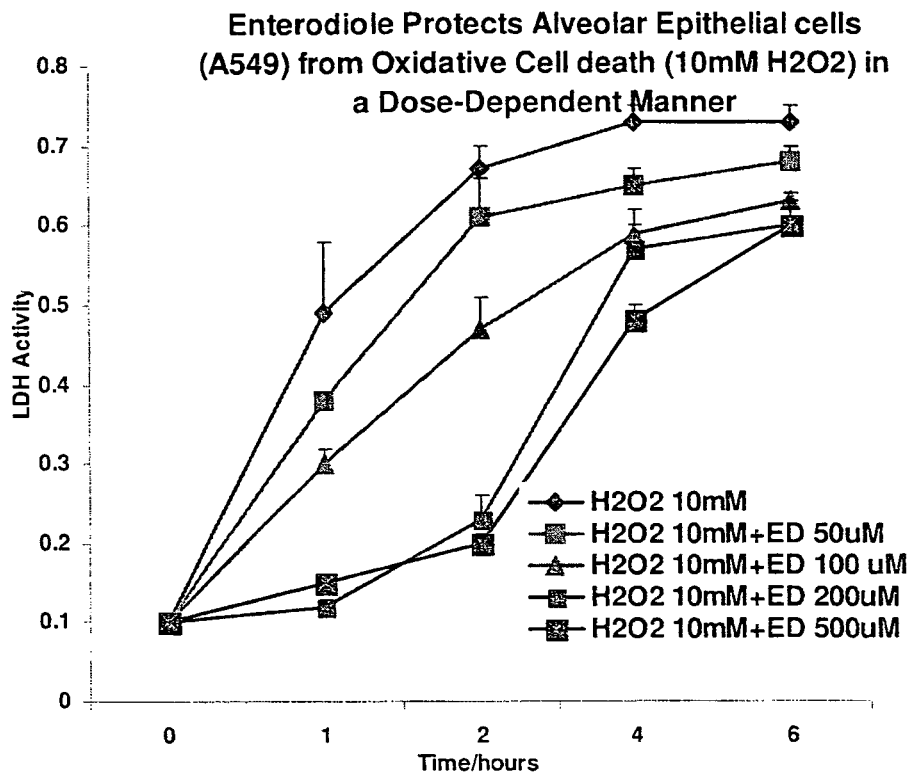
FIG. 20: shows that the chemically synthesized, commercially available lignan ED, significantly protects epithelial cells from cell death in a dose-dependent manner.

In addition, using the same assay system to detect cell death, LDH release, an evaluation of the efficacy of the lignan enterodiole, ED, to protect alveolar epithelial cells (A549) from oxidant-induced cell death was made. In these experiments, cells were pre-incubated with increasing concentrations of ED (10, 50, 100, 200, 500 uM) and challenged with hydrogen peroxide (10 mM H2O2) for 1-6 hours. ED, significantly protected epithelial cells from cell death in a dose-dependent manner. (FIG. 20).

These findings show that the flaxseed lignans can protect cells from oxidative stress-induced death.

Example 14: Chemically Synthesized Mammalian Flaxseed Lignans Reduce ROS Production by EC in Response to IRI (In Vitro)

Mouse. pulmonary endothelial cells (PMVEC) were grown on coverslips and placed in a Warner chamber and perfused with culture medium for 24 h at a flow rate of 10 dyn/cm$^2$. Cells were incubated with the Lignan ED (5 $\mu$M) for 5 h prior to I/R loaded with H2DCF to monitor ROS immediately before the experiment. I/R in this chamber is simulated by abrupt cessation of perfusate flow and its reinstatement through the chamber 5 minutes later. The images are in pseudocolor with intensity shown on the side bar. FIG. 21 shows a near complete abrogation of ROS generation by lignan-pre-treated EC (lack of yellow-red color).

Example 15: Flaxseed Lignans Act as Proteasomal Inhibitors

GFP$^u$-1 cells were used to investigate the impact of one of the flaxseed lignans, enterodiole (ED) on proteasomal activity. GFP$^u$-1 is an human kidney epithelial (HEK)-derived, stably transfected cell line expressing a short degron (CL1) tagged to green fluorescent protein (GFP) as described (ref). ED increased GFP levels in a dose-dependent fashion, a robust indication of proteasomal inhibition as shown by anti-GFP immunoblotting.

Figure 29:
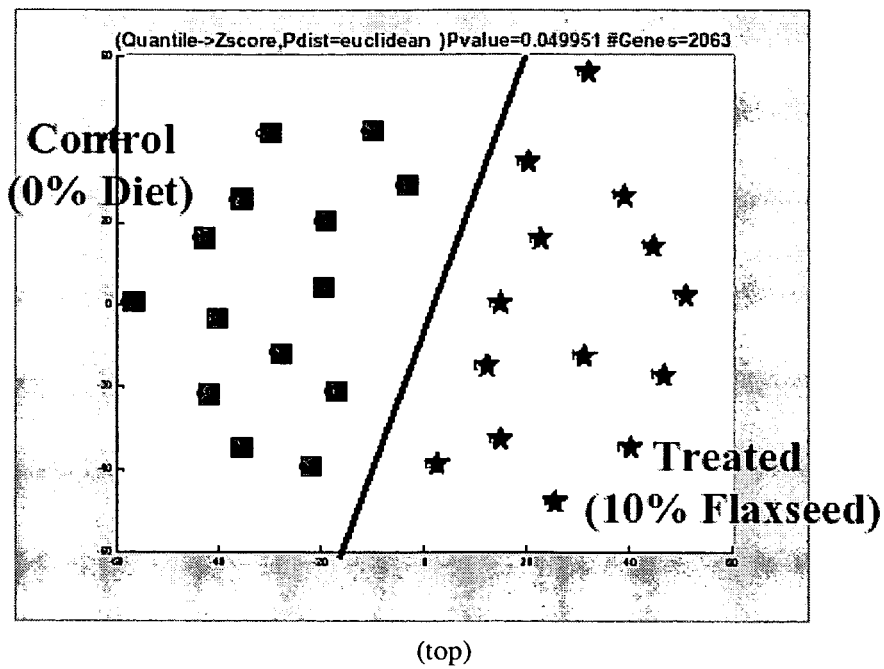
FIG. 29: shows a microarray analysis of lung tissues following dietary whole-grain flaxseed supplementation (10%).
Figure 29:
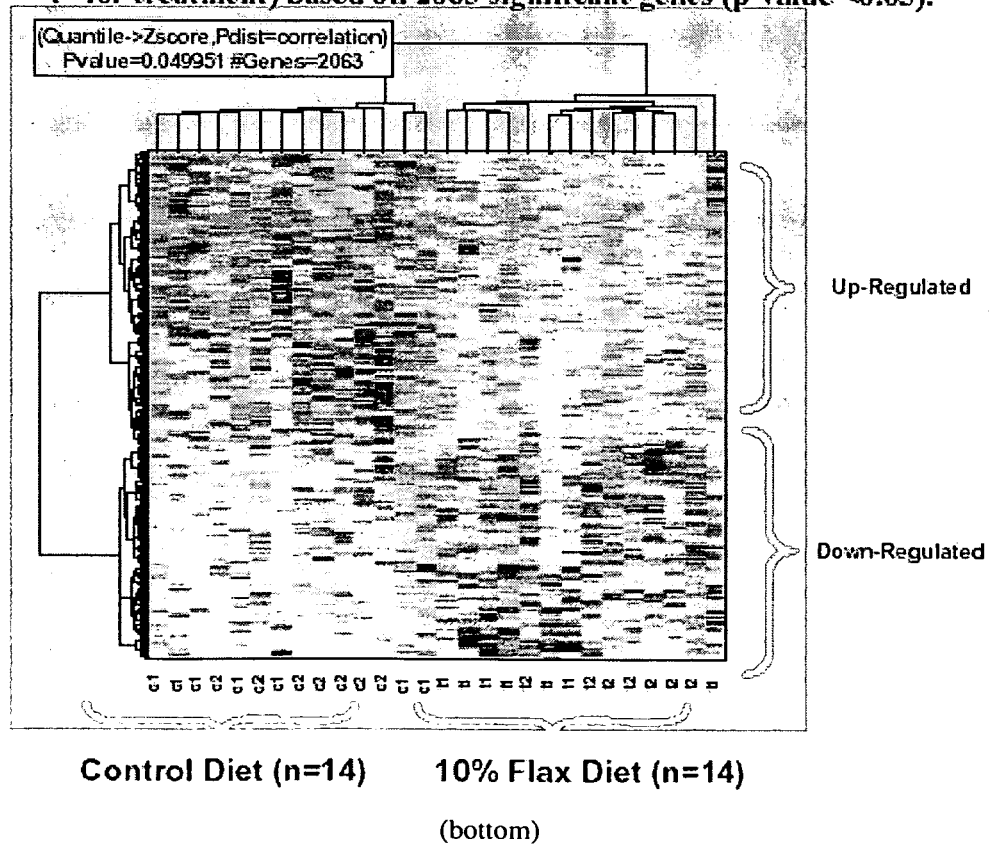

Microarray analysis of lungs from 14 control-diet fed and 14 flaxseed-fed mice (at least 3 weeks on the diet) was performed on 28,800 mouse genes. Analysis revealed 2063 statistically significant genes (p<0.05) modified by the FS diet. Top FIG. 29 shows the samples of the two classes (control diet vs. 10% FS) in two-dimensional space (Principle Component Analysis). Bottom FIG. 29 shows Hierarchical cluster analysis of the two classes (FS treatment and control), Taken with the findings of the protective effects of FS diet in radiation pneumonopathy, this data indicates that pre-feeding FS alters the expression of certain genes favoring abrogation of pro-inflammatory and pro-fibrogenic pathways. Importantly, FS may act on the tumor microenvironment blocking tumor growth and metastasis.

Figure 30:
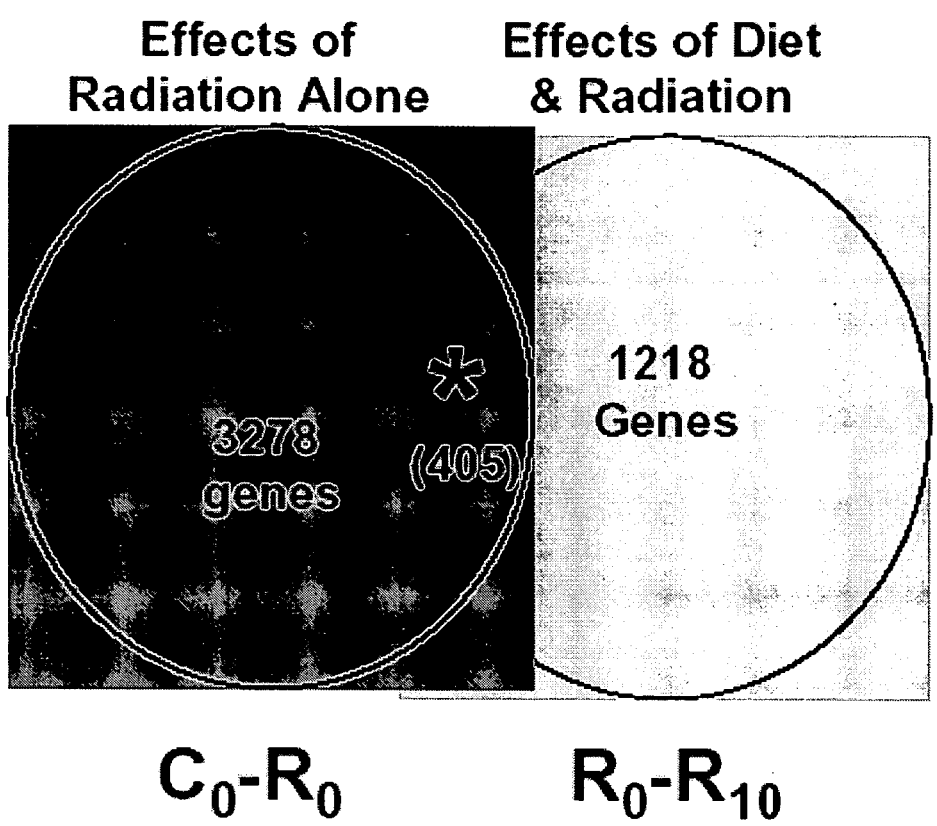
FIG. 30: Dietary Wholegrain Flaxseed (10%) Reversed Radiation-Induced Alterations of Gene Expression in Murine Lungs.

Gene changes were evaluated in lung tissues from irradiated mouse lungs given control or FS diet for 3 weeks, irradiated with a single fraction thoracic XRT (13.5 Gy) and lungs excised 48 hours post XRT. This generated 2 data sets shown in FIG. 30, one for irradiated 0% ($R_0$) and irradiated 10% FS ($R_{10}$). RNA was isolated and Microarray analysis performed for 28,800 mouse genes (n=6 mice/diet). Control, non-irradiated mouse lungs for each diet, gave rise to 2 additional data sets, namely control 0% ($C_0$) and control 10% FS ($C_{10}$) (n=14). Results indicated the following: R0-R10: Post radiation (48 hrs), mice have 1,218 genes that are differentially expressed due to both the diet and the radiation effects. C0-R0: Radiation alone induces 3,278 genes to be differentially expressed in mice fed a control diet.

The set of genes differentially expressed due to radiation alone that are also significantly changed due to the effects of FS diet post radiation (405 genes). Remarkably, of These Genes, 93% (378 genes) are reversed In Their Expression by FS. All genes are $p<0.05$.

Example 16: Dietary Flaxseed Prevents Tumor Growth

Figure 25:
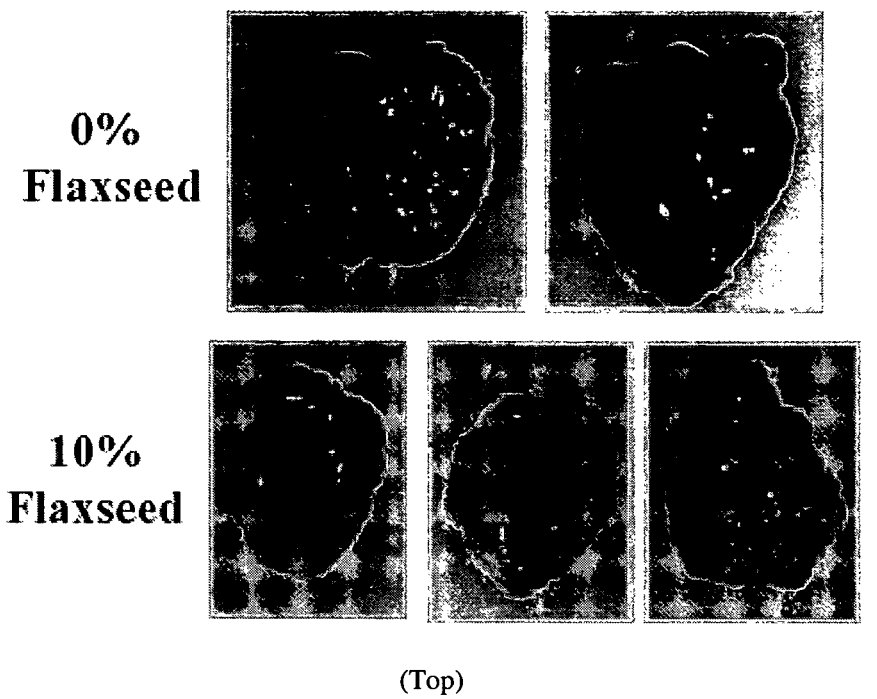
FIG. 25: shows that dietary flaxseed prevents lung tumor growth (% lung area occupied by tumor counted by image analysis software) and metastasis (number of tumor nodules) shown in clinical figure (top) and graph format (bottom).
Figure 25:
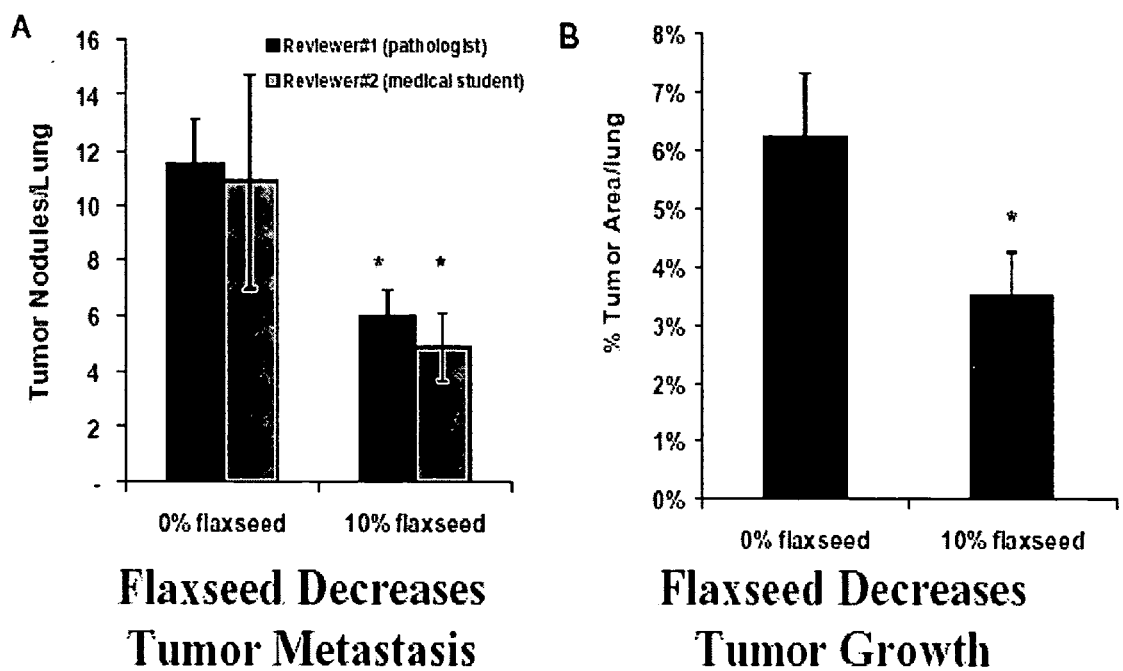

FIG. 25 shows that dietary flaxseed prevents lung tumor growth (% lung area occupied by tumor counted by image analysis software) and metastasis (number of tumor nodules) shown in clinical figure (left) and graph format (right): Lung cancer cell lines were injected iv in mice via tail vein ($1\times10^6$ cells) and tumor growth and metastasis was measured 3 weeks later. Tumor nodules were counted from histological lung sections blindly by a lung pathologist and a medical student. Results indicated a significant decrease in lung metastases by dietary supplementation of 10% FS initiated on the day of iv lung cancer cell injection.

Figure 32:
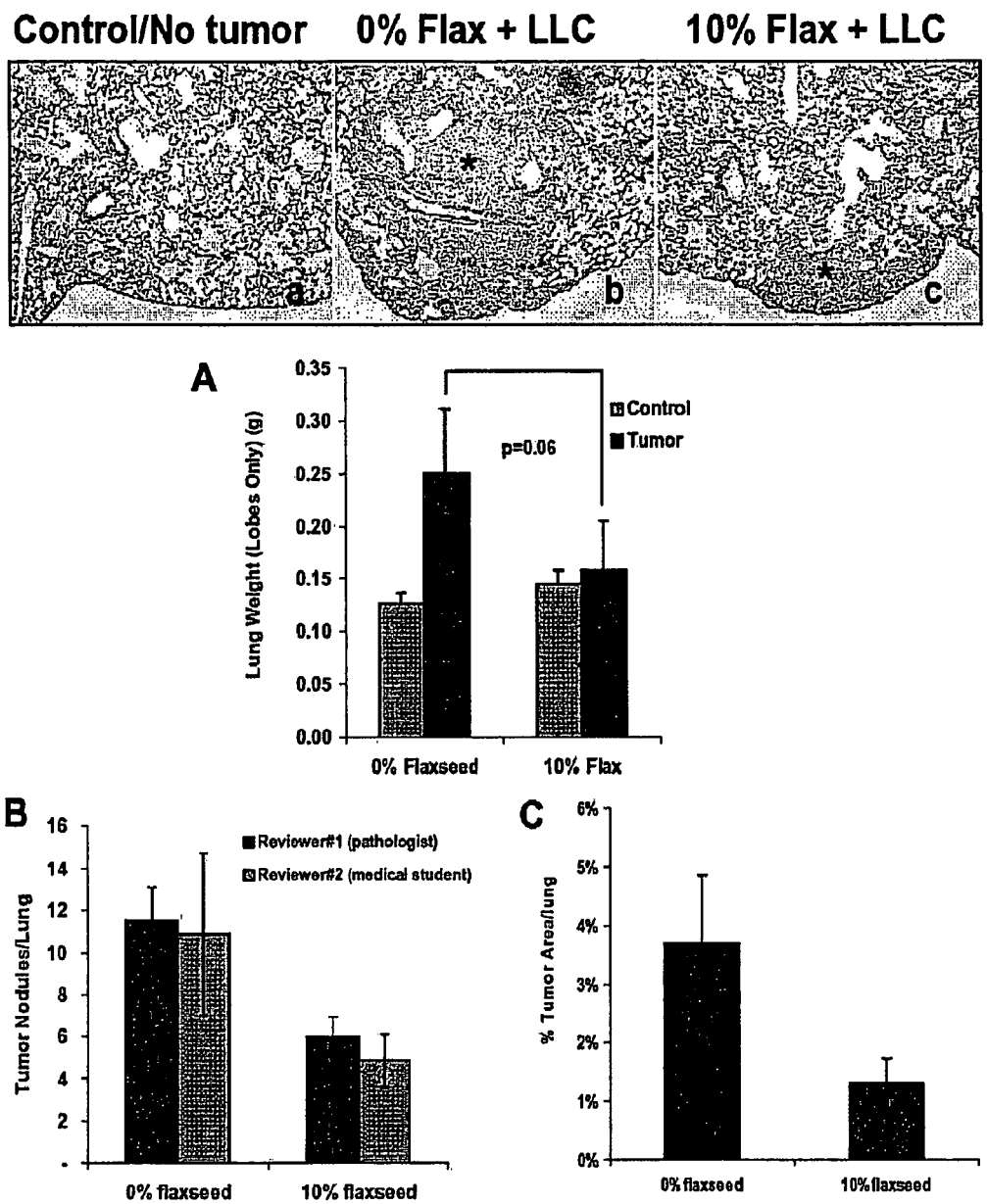
FIG. 32: Dietary Flaxseed reduces tumor metastasis and growth in mouse lungs. Mice were fed either a 0% or 10% FS supplemented diet for at least 3 weeks (n=10 mice/diet) were injected iv with 2 million LLC cells and lungs were excised and evaluated histologically with H&E staining, * represent tumor nodules. (Top panels). Overall tumor burden was assessed using lung weights (Panel A). Image analysis was performed for determination of tumor metastasis number (nodules/lung, Panel B), and overall tumor size (% tumor area/lung, Panel C).

Dietary FS reduces tumor growth and metastases in mouse lungs Mice were fed for three weeks with 0% or 10% FS prior to the injection of $2\times10^6$ LLC cells intravenously. At 10 days post injection, mice were sacrificed from each treatment group, lungs were excised for histological evaluation (FIG. 32, Top panels). Lungs were also weighed as an assessment of overall tumor burden (FIG. 32, Panel A). There was no significant difference in overall mouse weight (mean weight $19.3\pm0.25$ vs. $19.8\pm0.30$ grams in 0% FS and 10% FS fed mice, respectively). Histological analysis was performed by two blinded, independent reviewers to measure tumor nodules. There was a significant decrease in tumor nodules in the FS fed group (FIG. 32, Panel B). The percent tumor area per lung was also measured. There was a significant decrease in % tumor area in the 10% FS supplemented group, again suggesting overall decreased tumor burden from lung metastases (FIG. 32, Panel C).

Lung tumor burden was also decreased by FS diet as evidenced by lung weight measurements. This was also evidenced by clinical observation of the excised lungs. This provides the first evidence that flaxseed inhibits lung cancer tumor growth and metastasis.

Figure 26:
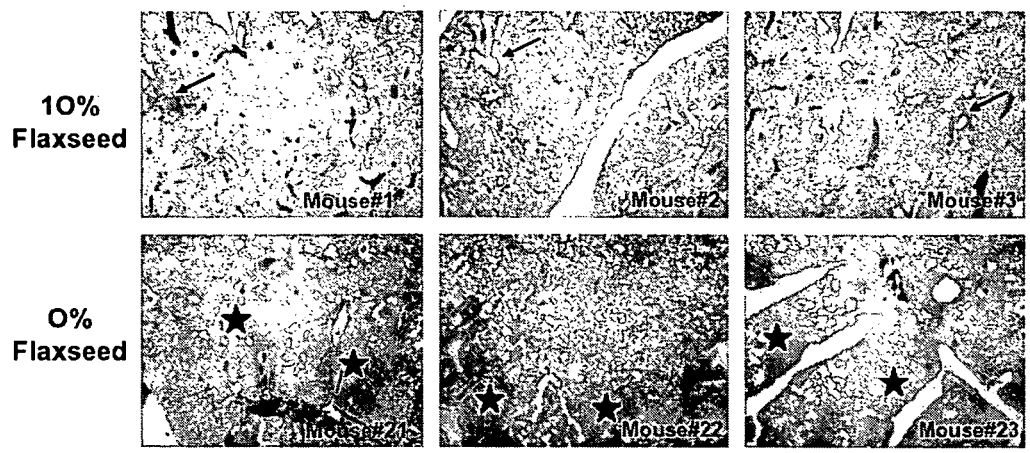
FIG. 26: shows that Dietary Whole Grain Flaxseed (10%) is highly effective in a murine orthotopic model of bronchogenic adenocarcinoma of the lung.
Figure 26:
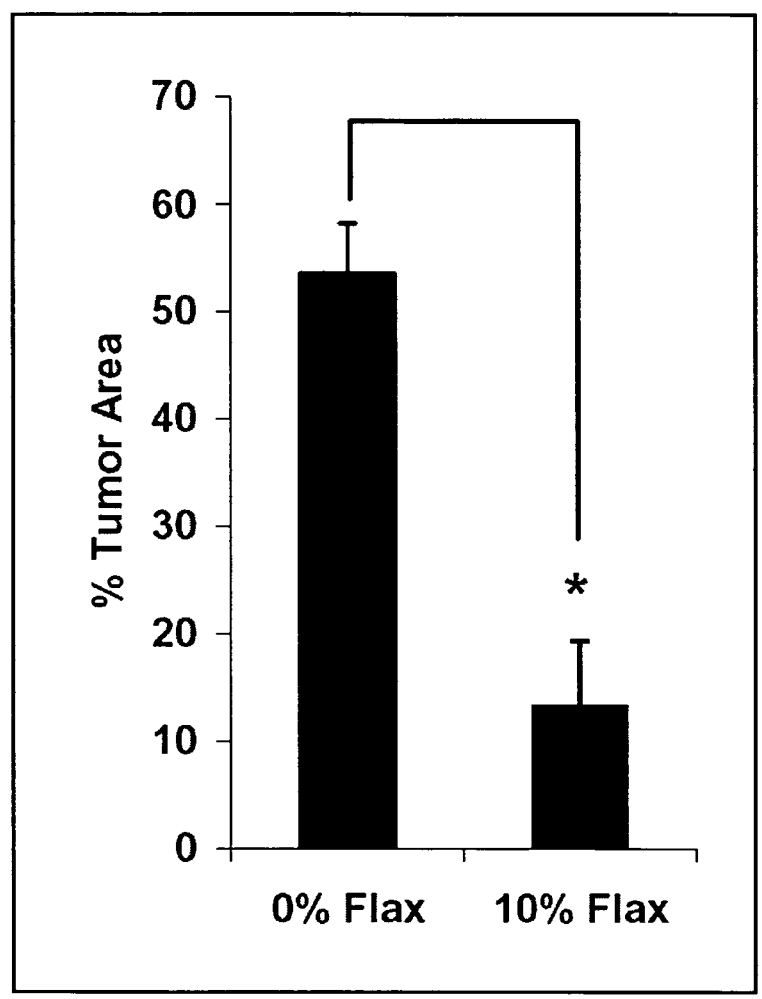
Figure 27:
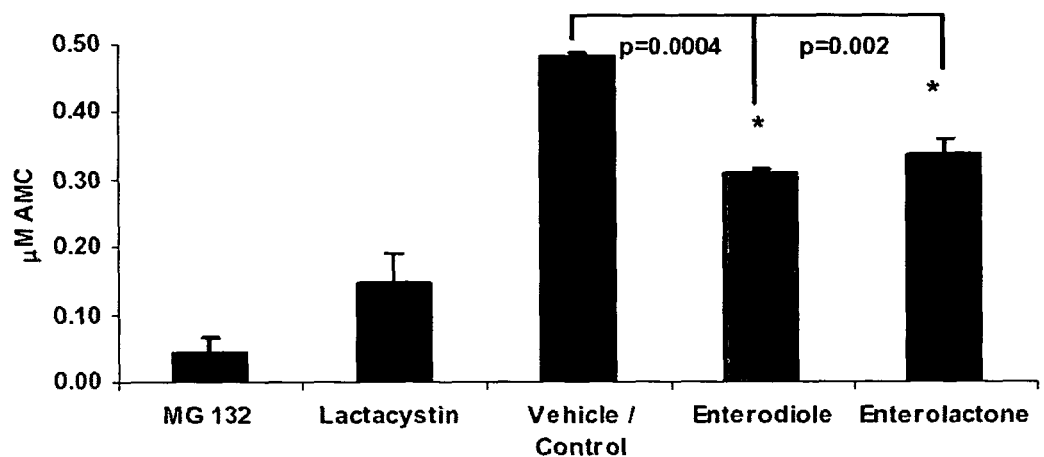
FIG. 27: shows how synthetic Flaxseed Lignans Act as Proteasomal Inhibitors when Incubated with Murine Cells in Culture.
Figure 28:
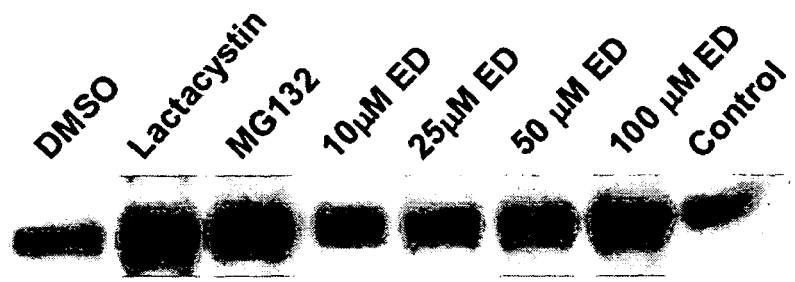
FIG. 28: shows how synthetic Flaxseed Lignan enterodiole (ED) Acts as Proteasomal Inhibitor in a dose dependent fashion when incubated with epithelial Cells in Culture.

As shown in FIG. 26, Mice were injected intratracheally with X109 Ad.Cre virus particles to initiate tumor formation and diet was initiated (0% vs. 10% Flaxseed) on the same day (n=20 per diet). Three (3) mice from each diet (Mouse 1-3 from 10% Flaxseed and mouse 21-23 from the 0% flaxseed diet) were sacrificed a month post tumor initiation for histopathological assessment. Mice fed whole-grain flaxseed had significantly less lung cancer burden shown histologically (top figure) and by measurement of tumor area (57% tumor in controls vs. 13% with FS) using image analysis software (bottom graph).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

Example 17: Dietary FS Inhibits Lung Tumor Growth in the Flanks of Mice

Figure 31:
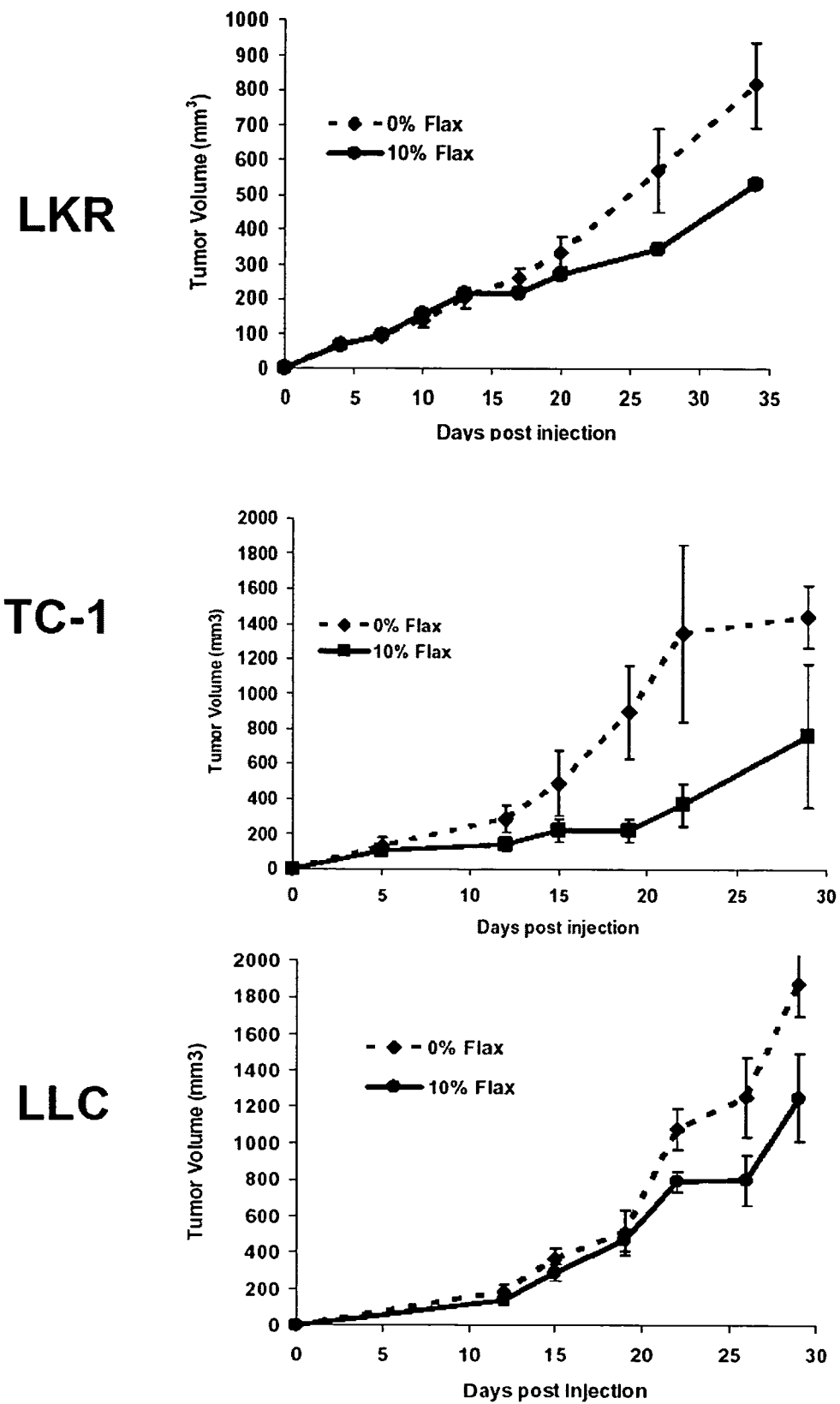
FIG. 31: Dietary Flaxseed inhibits lung tumor growth in the flanks of mice. 10% FS in the diets of mice given 3 weeks prior to the injection of 2 million lung cancer cells (Kras-derived LKR, TC-1, and LLC) in the flanks of mice was evaluated. Mice were kept on the diets for an additional 2-4 weeks and tumor size was evaluated every 3-4 days. Values represent means of 5 tumors±SEM.

Mice were fed for three weeks with 0% or 10% FS prior to the injection of $2\times10^6$ lung cancer cells (Kras-derived LKR, TC-1, LLC, AB-12, or L1C2) into the flanks of mice (n=? mice per diet per tumor line). Control and treatment diets were continued for the duration of the experiment (4-5 weeks post flank injection). Tumor size was evaluated every 3-4 days with volume determinations (FIG. 31). In three of the five cell lines tested (LKR, TC-1, and LLC), there was a significant decrease in rate of tumor growth and volume by approximately three weeks post flank injection.

Example 18: Dietary FS Reduces Tumor Growth in Mouse Lung in Tobacco Carcinogen-Induced Lung Cancer Briefly, A/J mice were injected i.p. with B[a]P (1 µg) for 3 weeks (once weekly). As controls, mice were injected with tricapryllin, the solvent/vehicle used for the B[a]P injections. Mice were placed on a 10% flaxseed-supplemented diet or a 0% Flaxseed, control diet from initiation of B[a]P injections. Mice were harvested 5 months post initiation of the injections and lungs evaluated histologically for tumor formation (n=5 mice per diet). Additional animals will be sacrificed at 6, 7, and 9 months post B[a]P.

Figure 33:
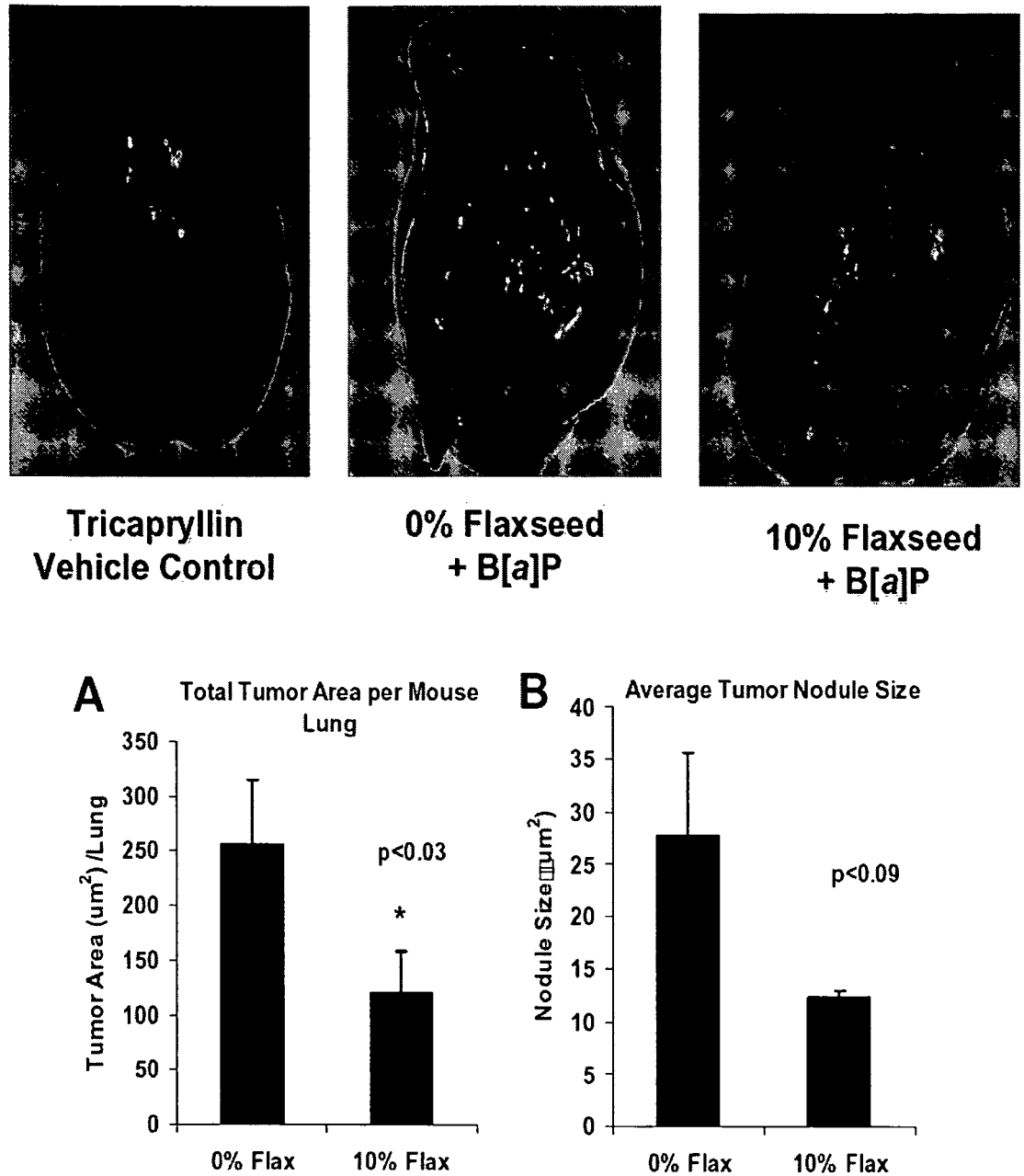
FIG. 33: Flaxseed abrogates B[a]P-induced lung nodule growth. All mice were injected with 4 weekly doses of 1 mg/mouse of B[a]P and lungs were evaluated 6 months later for tumor burden. Lung tissue sections (H&Es) were quantitatively assessed after 5 months for tumor. Panel A: Total tumor area per mouse (mm2); Panel B: Nodule size/area (mm2). Values are given as mean±SEM. Sample size=5 mice/group.
Figure 34:
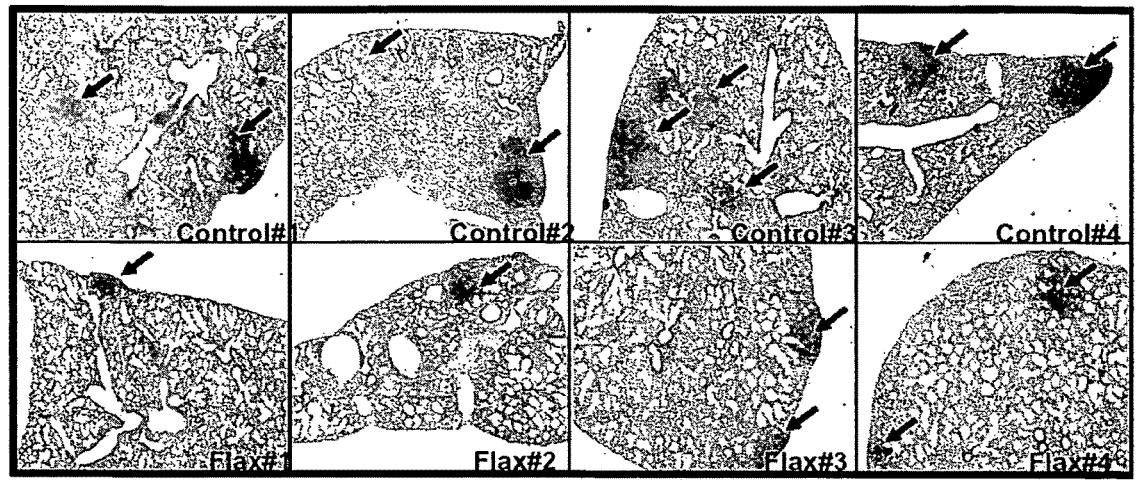
FIG. 34: Lung tumor volume is decreased with flaxseed. Histological views of control (top row) and flaxseed-fed (bottom row) lungs, 6 months post B[a]P injections (100×). Panel A: Tumor multiplicity (nodules/lung); Panel B: Percent Tumor Infiltrate (% tumor invading lungs). Values are given as Average±SEM. Sample size=5 mice/group.
Figure 34:
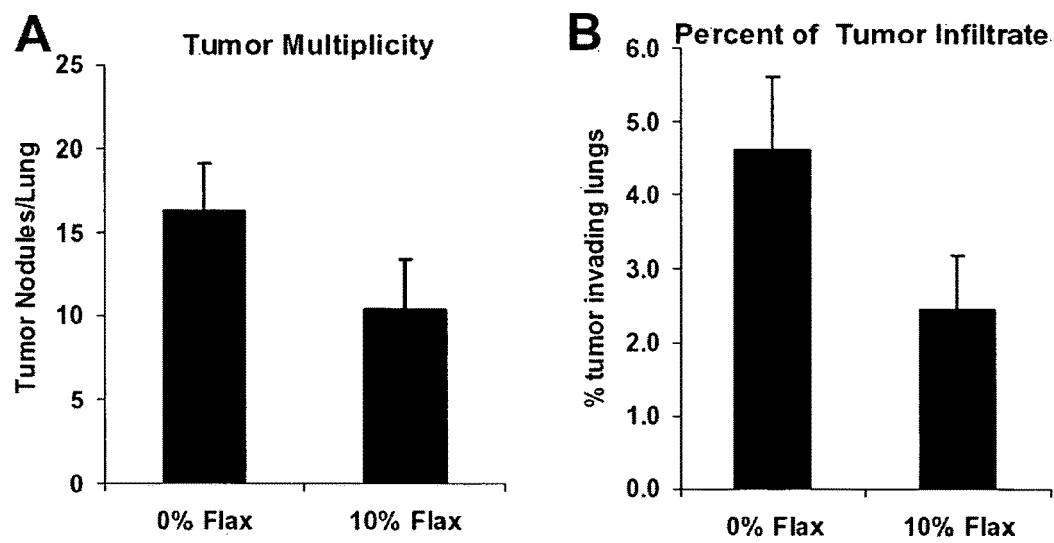

FIGS. 33 and 34 show representative, clinical and histological views, respectively, of mouse lungs from mice fed a 0% control diet vs. mice fed a 10% flaxseed-supplemented diet. Tumor incidence was 100% for both 0% and 10% Flaxseed diet. However, qualitatively, the tumor nodules appeared much smaller in lungs from the 10% flaxseed-fed mice. Indeed, quantification of tumor area using Phase 3 Image analysis software indicated that there was a significant decrease in overall tumor area ($p<0.03$) and a trend towards decreased individual nodule size ($p<0.09$) with flaxseed supplementation. This is indicated in FIG. 33, Panels A and B, respectively. Since % of lung area infiltrated by tumor is just $4.6\%\pm1\%$ for 0% flaxseed and $2.4\%\pm0.8\%$ for 10% flaxseed, i.e., still very small 5-6 months post injection of B[a]P, this trend may be further enhanced as tumor burden increases.

In Summary, this data provides robust evidence that a) the selected dose and mode of administration of B[a]P generates a reproducible lung carcinogenesis model and b) that flaxseed supplementation seems to retard lung tumor growth and incidence (FIG. 34).

Figure 35:
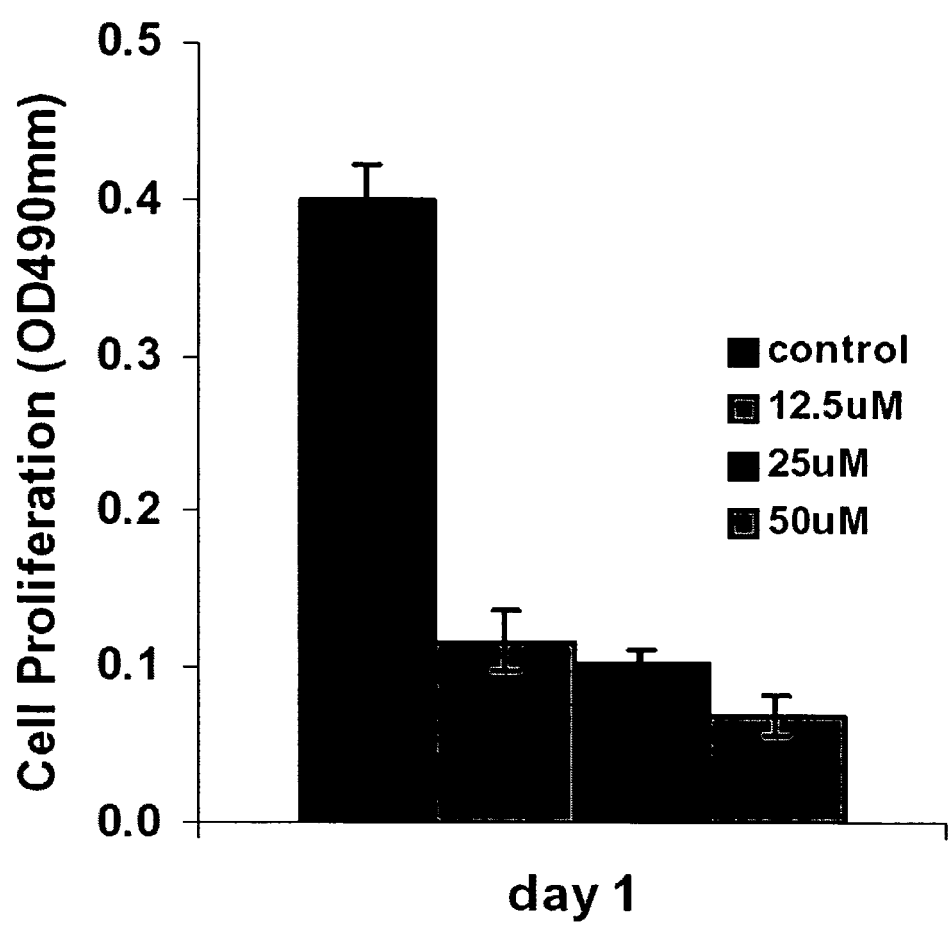
FIG. 35: Cancer cell proliferation is inhibited by a known pharmacological proteasome inhibitor. LKR cells were incubated with MG 132, a known pharmacological proteasomal inhibitor and cell proliferation was measured using the MTS assay at one day post incubation. There was a dose dependent decrease in cell proliferation with increasing doses of MG 132.

Example 19: Cancer Cell Proliferation is Inhibited by Known Proteasomal Inhibitor LKR cells derived from an explant of a pulmonary tumor from an activated K-rasG12D mutant mouse were incubated with differing concentrations of MG 132, a known pharmacological proteasomal inhibitor to assess for cell proliferation using the MTS assay. As seen in FIG. 35, there was a clear dose dependent response of MG 132 with increasing cell proliferation inhibition.

Example 20: Flaxseed Lignans EL and ED Exhibit Proteasomal Inhibition

Figure 36:
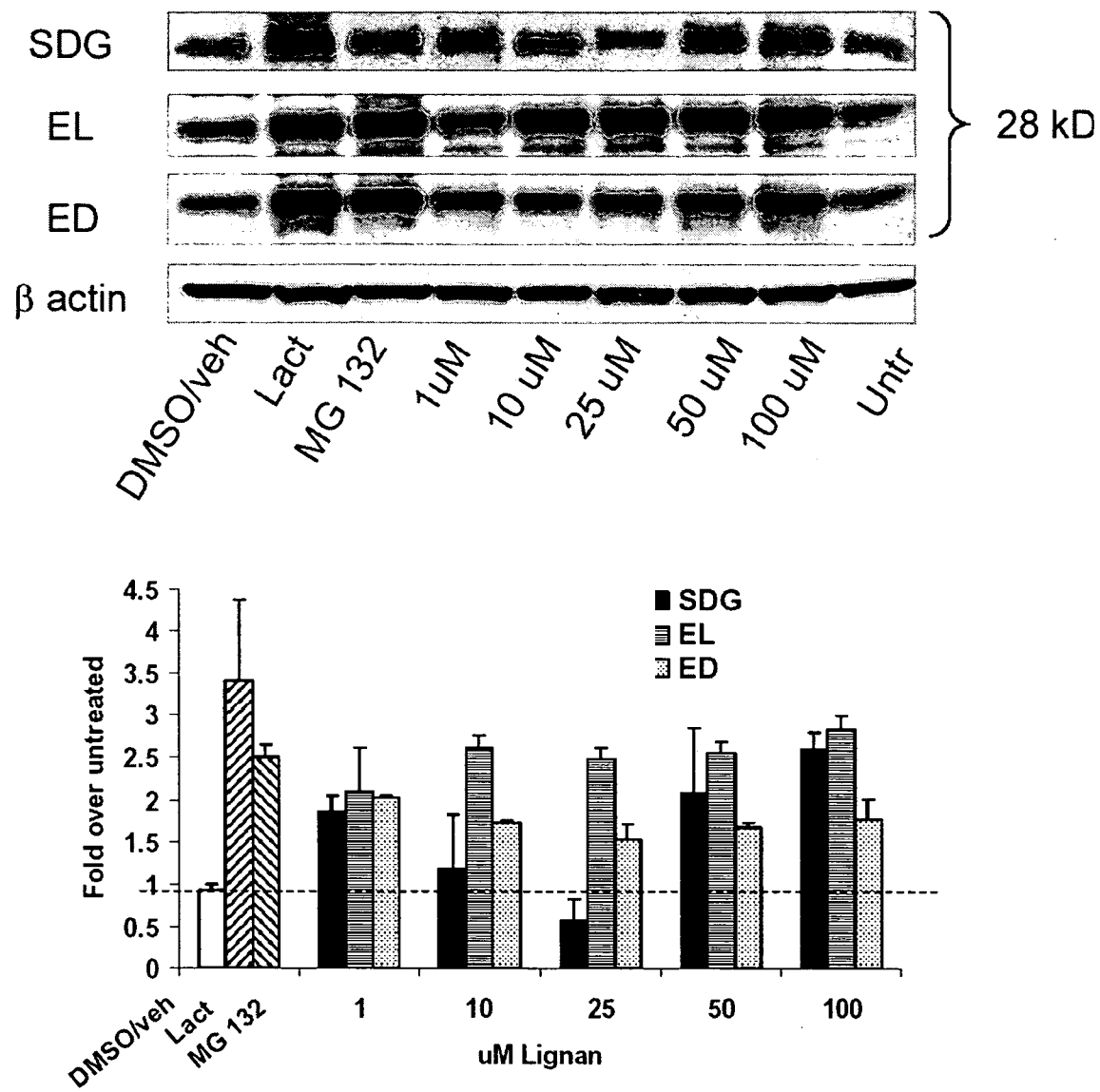
FIG. 36: Proteasomal inhibition with EL and ED as compared to known pharmacologic inhibitors Lactacystin and MG 132. GFPu-1 kidney epithelial cells were treated for 16 hours with EL and ED at differing concentrations. Proteasomal inhibition was detected by Western blotting using anti-GFP antibody with increased proteasomal inhibition expressed as accumulation of GFP. Representative Western blots are shown with β actin reference (Top panels). Densitometry was performed with β actin normalization, expressed as fold over untreated control±SEM, n=2-6 (Bottom panel). Dotted line represents control expression of GFP. *p<0.005 vs. untreated, **p<0.01 vs. untreated.

Using an in vitro means of quantifying proteasomal inhibition with GFPu-1 cells, differing concentrations of the FS lignans EL and ED were compared with known pharmacologic proteasomal inhibitors MG 132 and Lactacystin, incubated for 16 hours prior to processing. Western blotting was performed on whole Flaxseed and Lung Cancer cell lysates using anti-GFP antibodies to quantify the amount of GFP expressed as a marker of the amount of proteasomal inhibition (FIG. 36, Top panels). After densitometry analysis, in all concentrations of EL tested (1 µM to 100 µM), there was a significant increase in proteasomal inhibition compared to untreated cells as seen with increased GFP expression, and no significant difference in the amount of proteasomal inhibition as compared to Lactacystin and MG 132. In the concentrations of ED tested, there was again a significant amount of proteasomal inhibition compared to untreated cells, but the amount of proteasomal inhibition achieved was comparable to only Lactacystin, not MG 132 (FIG. 36, bottom panels).

Example 21: FS Lignans Inhibit Cell Proliferation of Lung Tumor Cell Lines

Figure 37:
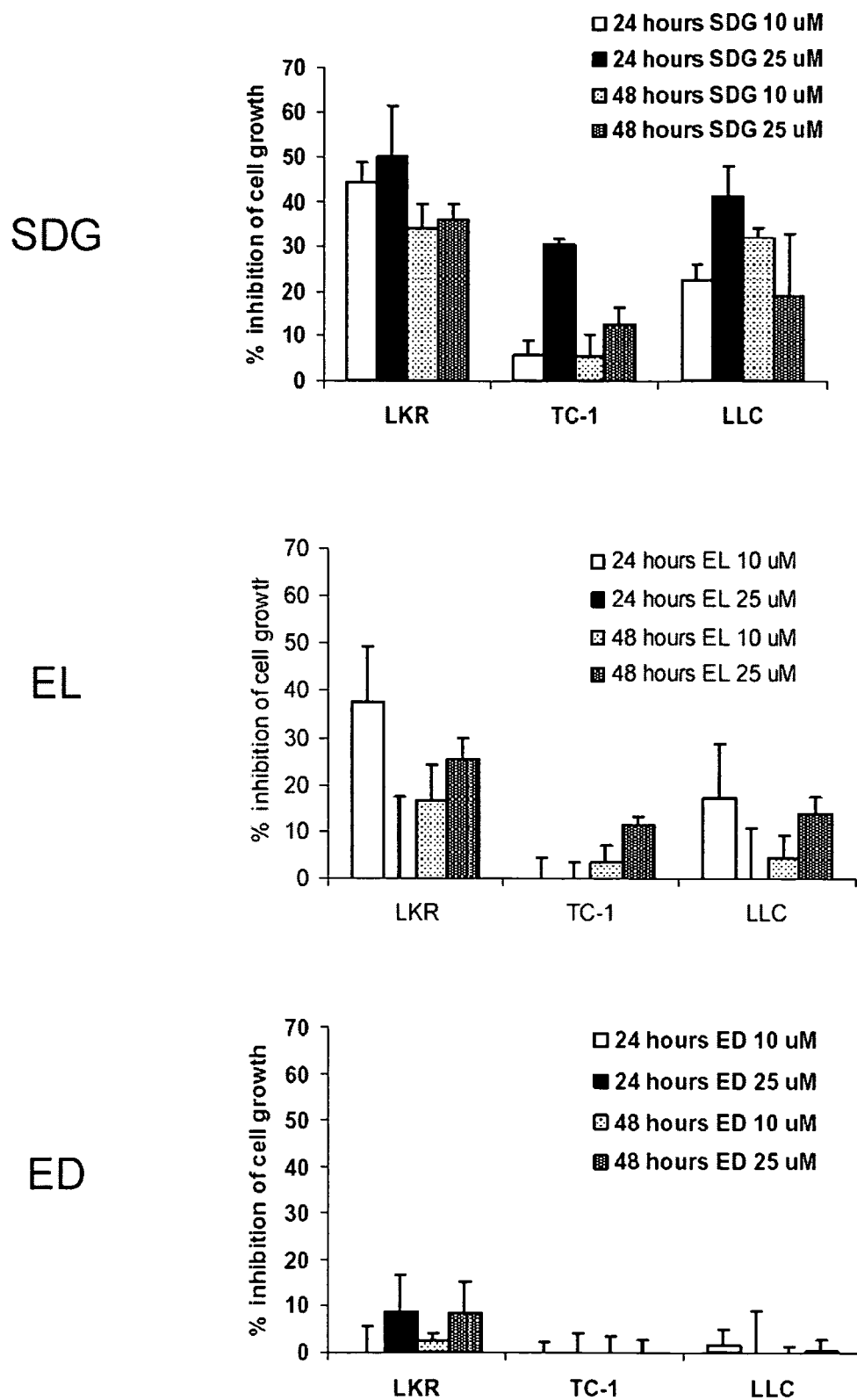
FIG. 37: FS lignans EL and ED, and their precursor SDG, inhibit cell proliferation in tumor cell lines. Tumor cell lines (LKR, TC-1, and LLC) were incubated with 10 µM or 25 µM of SDG, EL, or ED for 16 hours and processed for MTS assay to measure cell proliferation. The % inhibition of cell growth compared to untreated (no lignan) cell lines was calculated. Bars represent means±SEM. n=3 readings per group.

The three cell lines that showed a response to FS feeding in our flank model were incubated with the FS lignans SDG, EL, and ED at 10 µM for 16 hours. Cell proliferation was assessed at this time (time 0), and 24 and 48 hours later. As seen in FIG. 37, flaxseed lignans ED and El and the lignan precursor SDG induce a significant decrease of cancer cell proliferation rate when given at physiological doses (micromolar concentrations).

Thus wholegrain flaxseed diet has potent chemopreventive properties making this dietary agent an attractive candidate in lung cancer chemoprevention.

What is claimed is:

1. A method of reducing chronic lung fibrosis in a human subject comprising administering to a human subject having chronic lung fibrosis a composition comprising a therapeutically effective amount of a purified or chemically synthesized lignan, wherein said lignan is secoisolariciresinol diglucoside (SDG).

2. The method of claim 1, wherein the lung fibrosis is the result of acute lung injury.

3. The method of claim 1, wherein the chronic lung fibrosis is the result of an ischemia-reperfusion injury.

4. The method of claim 1, wherein the chronic lung fibrosis is the result of irradiation to the lung.

5. A method of reducing acute lung inflammation in a human subject comprising administering to a human subject having acute lung inflammation a composition comprising a therapeutically effective amount of a purified or chemically synthesized lignan, wherein said lignan is secoisolariciresinol diglucoside (SDG).

* * * * *